United States Patent
Hussain et al.

(10) Patent No.: US 10,621,394 B2
(45) Date of Patent: Apr. 14, 2020

(54) MODULAR RFID TRACKING USING PROBE

(71) Applicant: MEPS Real-Time, Inc., Carlsbad, CA (US)

(72) Inventors: Shariq Hussain, Vista, CA (US); Paul M. Elizondo, II, Escondido, CA (US)

(73) Assignee: MEPS Real-Time, Inc., Carlsbad, CA (US)

( * ) Notice: Subject to any disclaimer, the term of this patent is extended or adjusted under 35 U.S.C. 154(b) by 2 days.

(21) Appl. No.: 16/154,694

(22) Filed: Oct. 8, 2018

(65) Prior Publication Data

US 2019/0122013 A1 Apr. 25, 2019

Related U.S. Application Data

(63) Continuation of application No. 15/050,382, filed on Feb. 22, 2016, now Pat. No. 10,095,893, which is a (Continued)

(51) Int. Cl.
*G06K 7/10* (2006.01)
*G06F 19/00* (2018.01)
(Continued)

(52) U.S. Cl.
CPC ......... *G06K 7/10178* (2013.01); *G06F 19/00* (2013.01); *G06F 19/30* (2013.01);
(Continued)

(58) Field of Classification Search
CPC ......... G06K 7/10178; G06K 19/07749; G06K 17/00; G06K 7/0008; G16Z 99/00;
(Continued)

(56) References Cited

U.S. PATENT DOCUMENTS 2,417,542 A 3/1947 Carter
3,443,247 A 5/1969 Fjerstad
(Continued)

OTHER PUBLICATIONS

International Search Report dated Jun. 28, 2012 from International Application No. PCT/US2011/063162 filed Dec. 2, 2011, 9 pages.

*Primary Examiner* — Ryan W Sherwin
(74) *Attorney, Agent, or Firm* — Thomas A. Runk; Brooks Kushman P.C.

(57) ABSTRACT

A retrofit self-contained RFID-enabling module for automatically identifying and tracking medical articles having RF tags located in a container having electrically-conductive walls includes a base having a probe mounted to the base for injecting activating rf energy into the container in which the module has been mounted. The base also includes a reader board that controls the probe between an injection mode, in which it injects RFID tag activation energy into the container to activate the tags on the medical articles, and a non-injecting mode during which the identification signals of the activated RFID tags on the medical articles can be read. The module is self-contained in that only power is needed to operate. The size of the module, including its components, is selected in relation to the size of the container so that the module may be "dropped into" the container.

21 Claims, 21 Drawing Sheets

Related U.S. Application Data continuation of application No. 14/691,563, filed on Apr. 20, 2015, now Pat. No. 9,268,978, which is a continuation of application No. 13/024,146, filed on Feb. 9, 2011, now Pat. No. 9,013,307, which is a continuation-in-part of application No. 12/631,861, filed on Dec. 7, 2009, now Pat. No. 8,384,545.

(60) Provisional application No. 61/302,912, filed on Feb. 9, 2010.

(51) Int. Cl.

| | | |
|---|---|---|
| *G06Q 50/24* | (2012.01) | |
| *G06Q 50/22* | (2018.01) | |
| *G06K 19/077* | (2006.01) | |
| *G06Q 10/08* | (2012.01) | |
| *G06Q 30/00* | (2012.01) | |
| *G16H 10/60* | (2018.01) | |
| *G16Z 99/00* | (2019.01) | |
| *H04Q 9/00* | (2006.01) | |
| *G06K 7/00* | (2006.01) | |
| *G16H 70/00* | (2018.01) | |
| *G16H 50/00* | (2018.01) | |
| *G16H 20/13* | (2018.01) | |

(52) U.S. Cl.
CPC ........ *G06F 19/326* (2013.01); *G06F 19/3462* (2013.01); *G06K 7/0008* (2013.01); *G06K 19/07749* (2013.01); *G06Q 10/087* (2013.01); *G06Q 30/00* (2013.01); *G06Q 50/22* (2013.01); *G06Q 50/24* (2013.01); *G16H 10/60* (2018.01); *G16H 20/13* (2018.01); *G16H 50/00* (2018.01); *G16H 70/00* (2018.01); *G16Z 99/00* (2019.02); *H04Q 9/00* (2013.01); *H04Q 2209/47* (2013.01)

(58) Field of Classification Search
CPC .... G06F 19/00; G06F 19/326; G06F 19/3462; G06F 19/30; G16H 20/13; G16H 50/00; G16H 70/00; G16H 10/60; H04Q 9/00; H04Q 2209/47; G06Q 30/00; G06Q 10/087; G06Q 50/22; G06Q 50/24
See application file for complete search history.

(56) References Cited

U.S. PATENT DOCUMENTS

| | | |
|---|---|---|
| 4,293,223 A | 10/1981 | Seaton |
| 4,349,798 A | 9/1982 | Podell et al. |
| 4,495,478 A | 1/1985 | Kwon et al. |
| 5,581,268 A | 12/1996 | Hirshfield |
| 5,936,527 A | 8/1999 | Isaacman et al. |
| 6,133,800 A | 10/2000 | Deng |
| 6,232,870 B1 | 5/2001 | Garber et al. |
| 6,304,182 B1 | 10/2001 | Mori et al. |
| 6,486,780 B1 | 11/2002 | Garber et al. |
| 6,677,857 B2 | 1/2004 | Bara et al. |
| 6,768,472 B2 | 7/2004 | Alexopoulos et al. |
| 6,996,543 B1 | 2/2006 | Coppersmith et al. |
| 7,155,306 B2 | 12/2006 | Haitin et al. |
| 7,178,729 B2 | 2/2007 | Shaffer et al. |
| 7,258,276 B2 | 8/2007 | Linton et al. |
| 7,293,705 B2 | 11/2007 | Linton et al. |
| 7,299,981 B2 | 11/2007 | Hickle et al. |
| 7,369,919 B2 | 5/2008 | Vonk et al. |
| 7,433,610 B2 | 10/2008 | Oyama |
| 7,448,544 B1 | 11/2008 | Louie et al. |
| 7,466,232 B2 | 12/2008 | Neuwirth |
| 8,313,024 B2 * | 11/2012 | Marino ................ G06Q 10/08 235/383 |
| 9,013,307 B2 | 4/2015 | Hussain et al. |
| 9,268,978 B2 | 2/2016 | Hussain et al. |
| 2004/0008123 A1 | 1/2004 | Carrender et al. |
| 2007/0001809 A1 | 1/2007 | Kodukula et al. |
| 2007/0001890 A1 | 1/2007 | Piasecki et al. |
| 2007/0150382 A1 | 6/2007 | Danilewitz |
| 2007/0257857 A1 | 11/2007 | Marino et al. |
| 2008/0018475 A1 | 1/2008 | Breed et al. |
| 2008/0093448 A1 | 4/2008 | de la Huerga |
| 2008/0094222 A1 | 4/2008 | Kaoru |
| 2008/0117048 A1 | 5/2008 | Rachwalski et al. |
| 2008/0129453 A1 | 6/2008 | Shanks et al. |
| 2008/0224831 A1 | 9/2008 | Arai et al. |
| 2008/0283596 A1 | 11/2008 | Ishida |
| 2009/0251293 A1 * | 10/2009 | Azevedo ................ G07G 1/009 340/10.1 |
| 2010/0010666 A1 | 1/2010 | Adams |

* cited by examiner

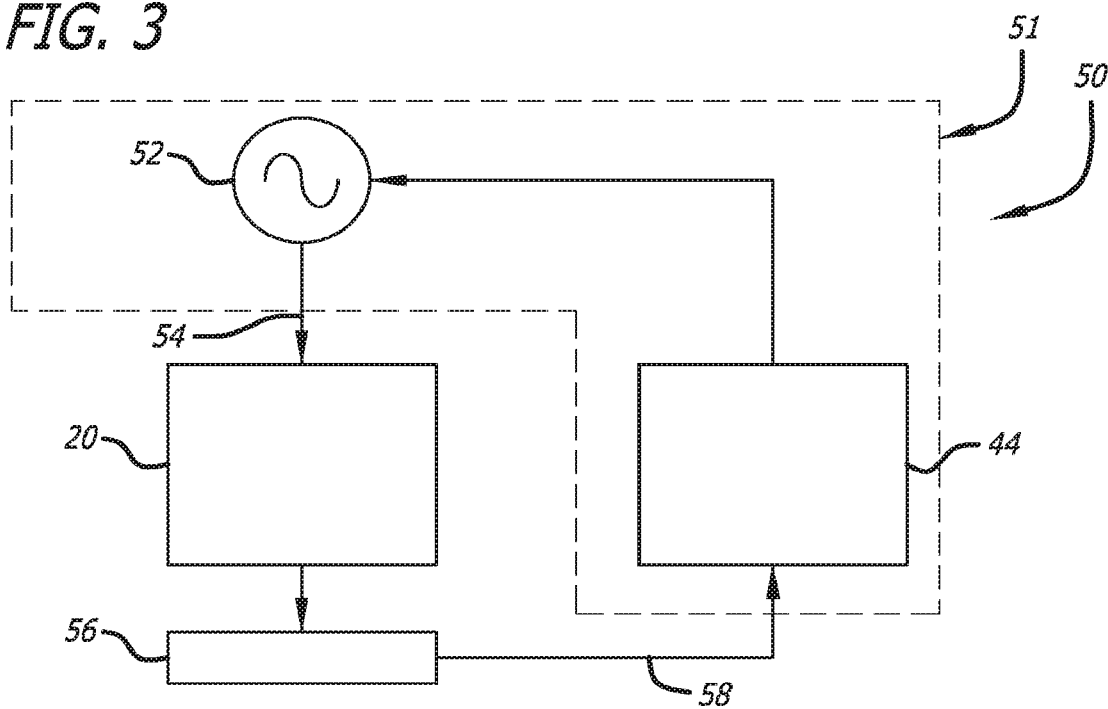
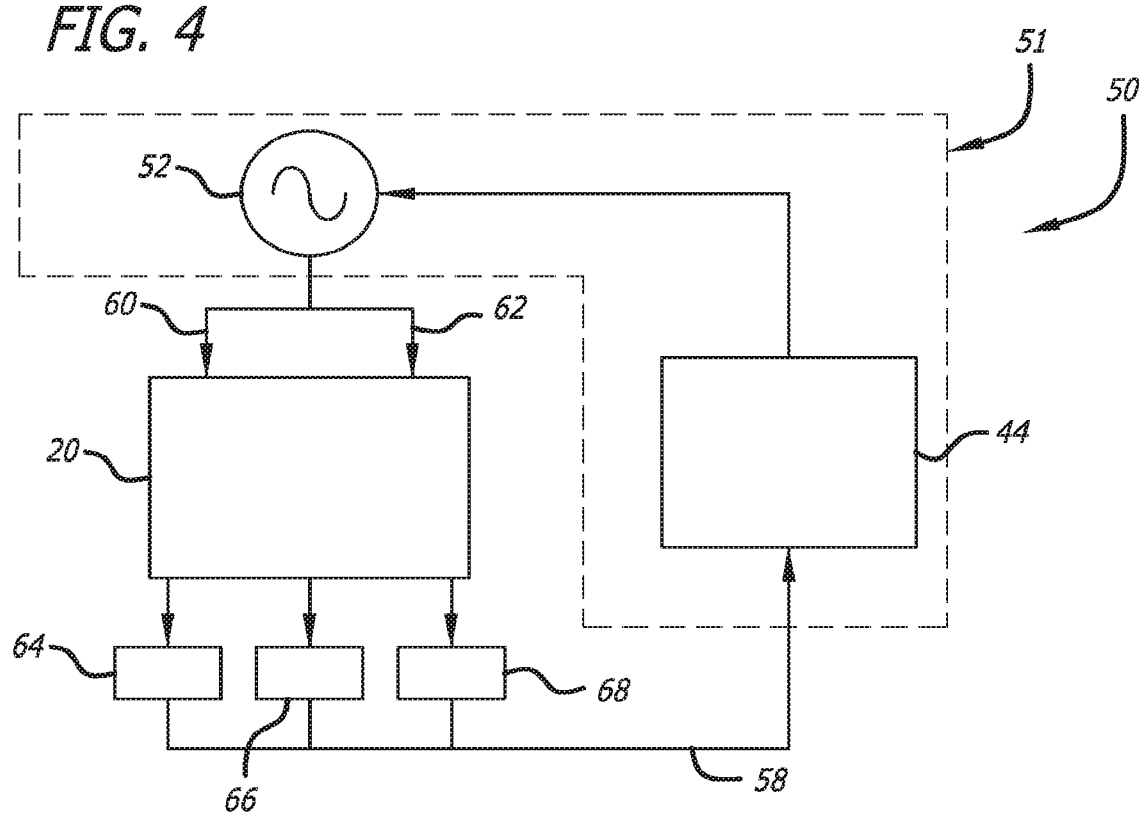

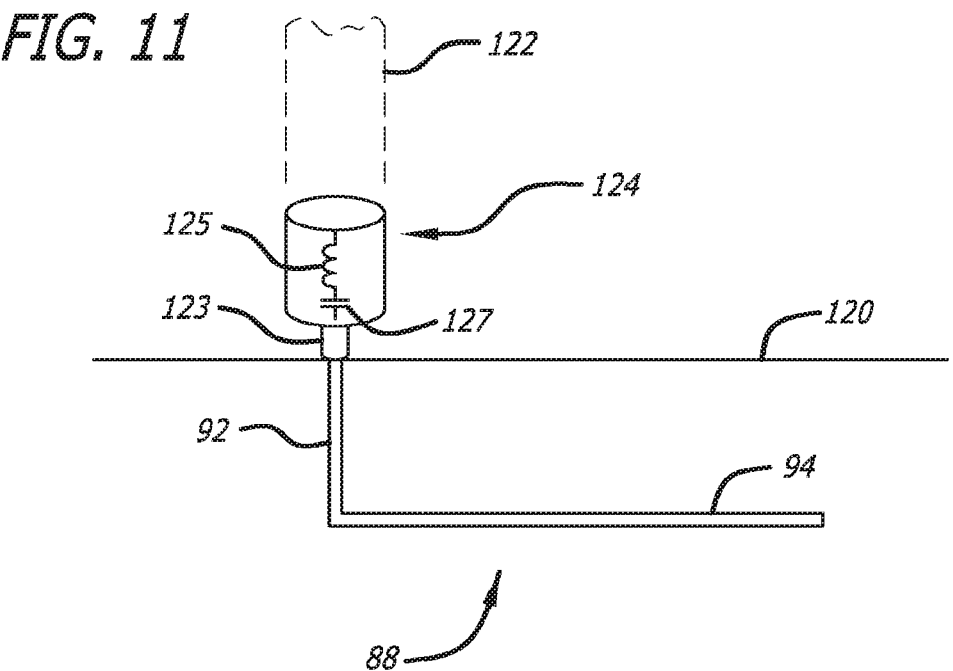
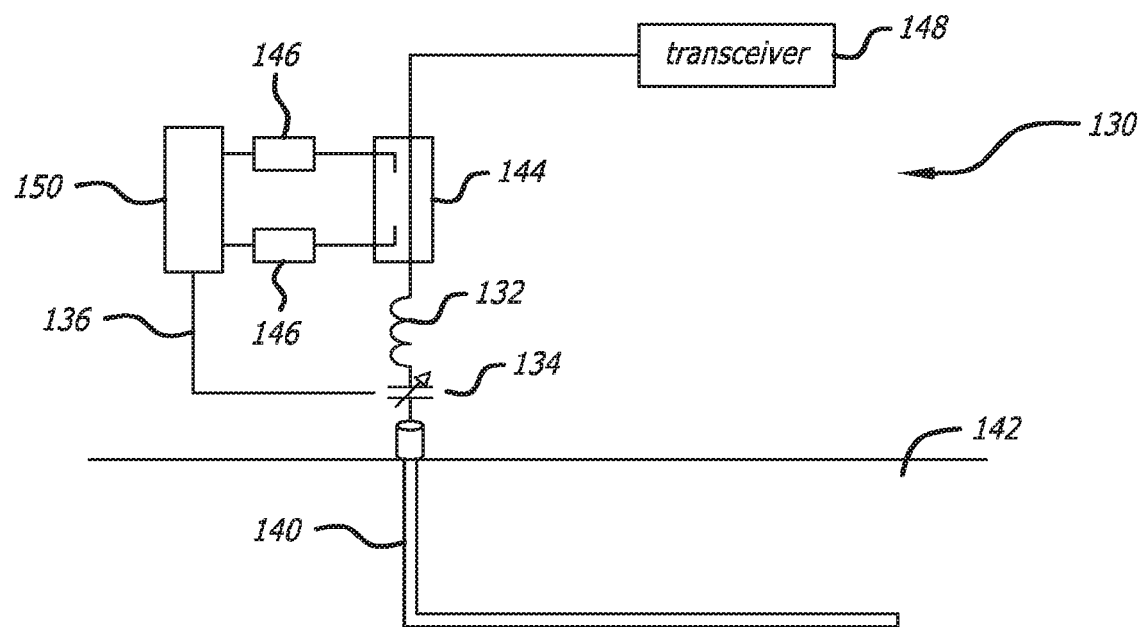

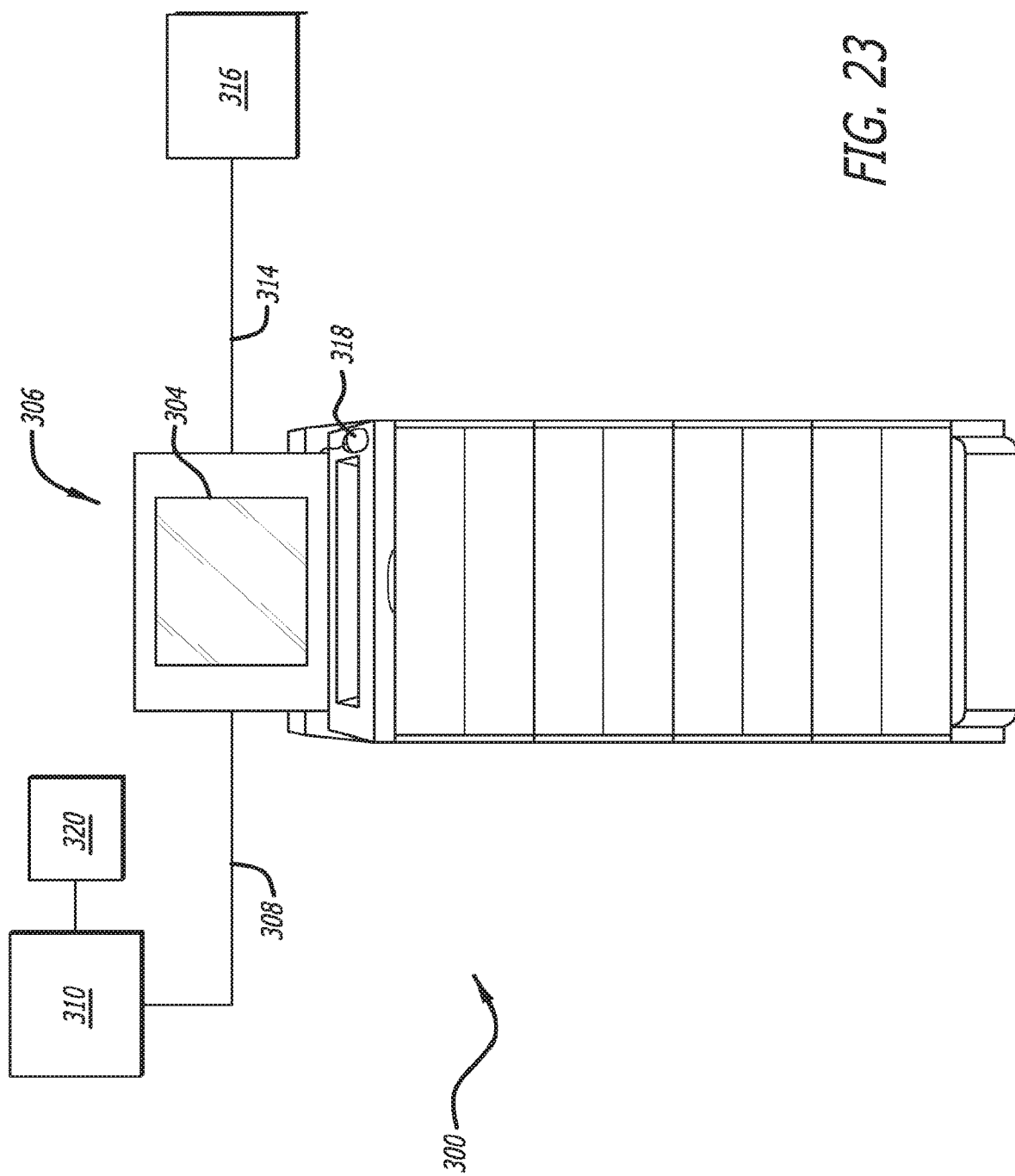

MODULAR RFID TRACKING USING PROBE

CROSS-REFERENCE TO RELATED APPLICATIONS

This application is a continuation of U.S. application Ser. No. 15/050,382, filed Feb. 22, 2016, now U.S. Pat. No. 10,095,893, which is a continuation of U.S. application Ser. No. 14/691,563, filed Apr. 20, 2015, now U.S. Pat. No. 9,268,978, which is a continuation of U.S. application Ser. No. 13/024,146, filed Feb. 9, 2011, now U.S. Pat. No. 9,013,307, which is a continuation-in-part of U.S. application Ser. No. 12/631,861, filed on Dec. 7, 2009, now U.S. Pat. No. 8,384,545, and which claimed benefit to U.S. Provisional Application No. 61/302,912, filed Feb. 9, 2010, all of which are incorporated by reference in their entirety.

BACKGROUND

The invention relates generally to the field of medication administration, and more particularly, to a medication administration system and associated method that provide identification, and tracking of medications in a container, such as a drawer.

Medication dispensing systems have been in use for many years. The initial purpose of such systems was to reduce medication errors associated with manual distribution and the high cost of maintaining a large amount of inventory. Current systems present many advantages, including lower costs associated with pharmaceutical distribution, improved inventory control, substance control, automated documentation, further reduction of errors, and relieving professional pharmacists and nursing personnel of many tasks.

In large medical facilities, the main inventories of pharmaceutical items are held in storage locations which are often far removed from the patients who use them. To facilitate secure and accurate delivery of the pharmaceutical items from these storage locations to the patient, a variety of systems have been proposed and put into use. In earlier systems, referred to as a "cart exchange" system, medication carts are distributed at nursing stations in the medical facility, remote from the central pharmacy, and are periodically exchanged with fully supplied carts. Typically, these carts contain a twenty-four hour supply of medications sorted by patient into specific drawers. The "used" cart is returned to a central pharmacy of supply area where the next twenty-four hours of medications are replenished. Narcotics are stored in locked boxes on the floor, requiring two nurses with separate keys and a written log.

While the cart exchange system is still in use for some medications, the activities of bringing up many new orders from the central pharmacy during the day, and having a large amount of unused medication being returned results in a large amount of labor. The re-stocking of these medications needs to be done accurately, and is very time consuming. As a result, there has been an increasing use of automated, processor-based, medication cabinets on the nursing floors. The processor on each cabinet monitors the access to the pharmaceutical items in these fixed cabinets, allowing the current on-hand inventory and the need for replenishment to be communicated to a central processor at the central pharmacy location. These processor-based dispensing cabinets were initially used for the more convenient management of narcotics, and for the ability to have a "floor stock" of common medications and other medical supplies from which a nurse could issue the first dose of a needed new prescription, while waiting for the twenty-four hours supply to be delivered from the pharmacy in the exchange cart, or on a special order basis.

Referring now to FIG. 23 the medication cabinet 300 typically comprises an integrated touch screen 304 coupled to a control unit 306, a communication link 308 for linking to a central server 310, and a communication link 314 for linking to one or more carts 316. Such communication links 308 and 314 are schematically shown as connections for wired communication, but could also be transmitters and receivers (e.g., RF, IR, acoustical) for wireless communication as would be recognized by one of ordinary skill in communication technologies. In addition to the data that is input via the communication links 308 and 314, data is input manually via a virtual keyboard included in the touch screen 304. Although not clearly shown, a keyboard may also be provided as well as the pointing device 318, which is shown. The keyboard and pointing device may take different forms. In one embodiment, the keyboard may be full size and in another embodiment, the keyboard may be compact. Similarly, the pointing device may be a mouse, touch pad, or other device. The communication link 308 is a connection to the server 310 and allows the medication cabinet 300 to interface with the data base 320 to which the server 310 has access for real-time updates, as needed. It also provides necessary information to guide the pre-authorized healthcare attendant in the preparation of patient medications, intravenous solutions, and the like. In an alternative embodiment shown in FIG. 24, a full size actual keyboard 322 or keypad is provided and may replace or augment the functions of the touch screen 304.

These processor-based medication cabinets 300 offer the possibility of storing the majority of medications that the patients on the floor might need during the day and night. In many cases, these medications are stored in pockets within locked drawers. A nurse, upon entering his or her own personal ID, and the ID of a specific patient, will see the medications that are approved overall for that selected patient and will also see what medications are due at that particular time, referred to generally as "Due Medications." The task for the central pharmacy then is to monitor the on-hand stock of the medications stored in the cabinets, and restock those levels at regular intervals. A significant advantage of this process is not having unused doses of medications returned to the central pharmacy. It also means that first doses (as well as subsequent doses) are immediately available.

The handling of medications has often been a manual process in determining which medications were removed from the cabinet and which remain. Such manual handling, examination, and research are time consuming. It would be desirable to provide a system and method that can automate at least some of these requirements so that efficiency is increased.

Radio-frequency identification ("RFID") is the use of electromagnetic energy ("EM energy") to stimulate a responsive device (known as an RFID "tag" or transponder) to identify itself and in some cases, provide additionally stored data. RFID tags typically include a semiconductor device having a memory, circuitry, and one or more conductive traces that form an antenna. Typically, RFID tags act as transponders, providing information stored in the semiconductor device memory in response to an RF interrogation signal received from a reader, also referred to as an interrogator. Some RFID tags include security measures, such as passwords and/or encryption. Many RFID tags also permit information to be written or stored in the semiconductor memory via an RF signal.

RFID tags may be incorporated into or attached to articles to be tracked. In some cases, the tag may be attached to the outside of an article with adhesive, tape, or other means and in other cases, the tag may be inserted within the article, such as being included in the packaging, located within the container of the article, or sewn into a garment. The RFID tags are manufactured with a unique identification number which is typically a simple serial number of a few bytes with a check digit attached. This identification number is incorporated into the tag during manufacture. The user cannot alter this serial/identification number and manufacturers guarantee that each serial number is used only once. This configuration represents the low cost end of the technology in that the RFID tag is read-only and it responds to an interrogation signal only with its identification number. Typically, the tag continuously responds with its identification number. Data transmission to the tag is not possible. These tags are very low cost and are produced in enormous quantities.

Such read-only RFID tags typically are permanently attached to an article to be tracked and, once attached, the serial number of the tag is associated with its host article in a computer data base. For example, a particular type of medicine may be contained in hundreds or thousands of small vials. Upon manufacture, or receipt of the vials at a health care institution, an RFID tag is attached to each vial. Each vial with its permanently attached RFID tag will be checked into the data base of the health care institution upon receipt. The RFID identification number may be associated in the data base with the type of medicine, size of the dose in the vial, and perhaps other information such as the expiration date of the medicine. Thereafter, when the RFID tag of a vial is interrogated and its identification number read, the data base of the health care institution can match that identification number with its stored data about the vial. The contents of the vial can then be determined as well as any other characteristics that have been stored in the data base. This system requires that the institution maintain a comprehensive data base regarding the articles in inventory rather than incorporating such data into an RFID tag.

An object of the tag is to associate it with an article throughout the article's life in a particular facility, such as a manufacturing facility, a transport vehicle, a health care facility, a storage area, or other, so that the article may be located, identified, and tracked, as it is moved. For example, knowing where certain medical articles reside at all times in a health care facility can greatly facilitate locating needed medical supplies when emergencies arise. Similarly, tracking the articles through the facility can assist in generating more efficient dispensing and inventory control systems as well as improving work flow in a facility. Additionally, expiration dates can be monitored and those articles that are older and about to expire can be moved to the front of the line for immediate dispensing. This results in better inventory control and lowered costs.

Other RFID tags are writable and information about the article to which the RFID tag is attached can be programmed into the individual tag. While this can provide a distinct advantage when a facility's computer servers are unavailable, such tags cost more, depending on the size of the memory in the tag. Programming each one of the tags with information contained in the article to which they are attached involves further expense.

RFID tags may be applied to containers or articles to be tracked by the manufacturer, the receiving party, or others. In some cases where a manufacturer applies the tags to the product, the manufacturer will also supply a respective data base file that links the identification number of each of the tags to the contents of each respective article. That manufacturer supplied data base can be distributed to the customer in the form of a file that may easily be imported into the customer's overall data base thereby saving the customer from the expense of creating the data base.

Many RFID tags used today are passive in that they do not have a battery or other autonomous power supply and instead, must rely on the interrogating energy provided by an RFID reader to provide power to activate the tag. Passive RFID tags require an electromagnetic field of energy of a certain frequency range and certain minimum intensity in order to achieve activation of the tag and transmission of its stored data. Another choice is an active RFID tag; however, such tags require an accompanying battery to provide power to activate the tag, thus increasing the expense of the tag and making them undesirable for use in a large number of applications.

Depending on the requirements of the RFID tag application, such as the physical size of the articles to be identified, their location, and the ability to reach them easily, tags may need to be read from a short distance or a long distance by an RFID reader. Such distances may vary from a few centimeters to ten or more meters. Additionally, in the U.S. and in other countries, the frequency range within which such tags are permitted to operate is limited. As an example, lower frequency bands, such as 125 KHz and 13.56 MHz, may be used for RFID tags in some applications. At this frequency range, the electromagnetic energy is less affected by liquids and other dielectric materials, but suffers from the limitation of a short interrogating distance. At higher frequency bands where RFID use is permitted, such as 915 MHz and 2.4 GHz, the RFID tags can be interrogated at longer distances, but they de-tune more rapidly as the material to which the tag is attached varies. It has also been found that at these higher frequencies, closely spaced RFID tags will de-tune each other as the spacing between tags is decreased.

There are a number of common situations where the RFID tags may be located inside enclosures. Some of these enclosures may have entirely or partially metal or metallized surfaces. Examples of enclosures include metal enclosures (e.g., shipping containers), partial metal enclosures (e.g., vehicles such as airplanes, buses, trains, and ships that have a housing made from a combination of metal and other materials), and non-metal enclosures (e.g., warehouses and buildings made of wood). Examples of objects with RFID tags that may be located in these enclosures include loose articles, packaged articles, parcels inside warehouses, inventory items inside buildings, various goods inside retail stores, and various portable items (e.g., passenger identification cards and tickets, baggage, cargo, individual life-saving equipment such as life jackets and masks) inside vehicles, etc.

The read range (i.e., the range of the interrogation and/or response signals) of RFID tags is limited. For example, some types of passive RFID tags have a maximum range of about twelve meters, which may be attained only in ideal free space conditions with favorable antenna orientation. In a real situation, the observed tag range is often six meters or less. Therefore, some of the enclosures described above may have dimensions that far exceed the read range of an individual RFID tag. Unless the RFID reader can be placed in close proximity to a target RFID tag in such an enclosure, the tag will not be activated and read. Additionally, metal surfaces of the enclosures present a serious obstacle for the RF signals that need to be exchanged between RFID readers and RFID tags, making RFID tags located behind those metal surfaces difficult or impossible to detect.

In addition to the above, the detection range of the RFID systems is typically limited by signal strength to short ranges, frequently less than about thirty centimeters for 13.56 MHz systems. Therefore, portable reader units may need to be moved past a group of tagged items in order to detect all the tagged items, particularly where the tagged items are stored in a space significantly greater than the detection range of a stationary or fixed single reader antenna. Alternately, a large reader antenna with sufficient power and range to detect a larger number of tagged items may be used. However, such an antenna may be unwieldy and may increase the range of the radiated power beyond allowable limits. Furthermore, these reader antennae are often located in stores or other locations where space is at a premium and it is expensive and inconvenient to use such large reader antennae. In another possible solution, multiple small antennae may be used but such a configuration may be awkward to set up when space is at a premium and when wiring is preferred or required to be hidden.

In the case of medical supplies and devices, it is desirable to develop accurate tracking, inventory control systems, and dispensing systems so that RFID tagged devices and articles may be located quickly should the need arise, and may be identified for other purposes, such as expiration dates. In the case of medical supply or dispensing cabinets used in a health care facility, a large number of medical devices and articles are located closely together, such as in a plurality of drawers. Cabinets such as these are typically made of metal, which can make the use of an external RFID system for identification of the stored articles difficult. In some cases, such cabinets are locked due to the presence of narcotics or other medical articles or apparatus within them that are subject to a high theft rate. Thus, manual identification of the cabinet contents is difficult due to the need to control access.

Providing an internal RFID system in such a cabinet can pose challenges. Where internal articles can have random placement within the cabinet, the RFID system must be such that there are no "dead zones" that the RFID system is unable to reach. In general, dead zones are areas in which the level of coupling between an RFID reader antenna and an RFID tag is not adequate for the system to perform a successful read of the tag. The existence of such dead zones may be caused by orientations in which the tag and the reader antennae are in orthogonal planes. Thus, articles placed in dead zones may not be detected thereby resulting in inaccurate tracking of tagged articles.

Often in the medical field, there is a need to read a large number of tags attached to articles in such an enclosure, and as mentioned above, such enclosures have limited access due to security reasons. The physical dimension of the enclosure may need to vary to accommodate a large number of articles or articles of different sizes and shapes. In order to obtain an accurate identification and count of such closely-located medical articles or devices, a robust electromagnetic energy field must be provided at the appropriate frequency within the enclosure to surround all such stored articles and devices to be sure that their tags are all are activated and read. Such medical devices may have the RFID tags attached to the outside of their containers and may be stored in various orientations with the RFID tag (and associated antenna) pointed upwards, sideways, downward, or at some other angle in a random pattern.

Generating such a robust EM energy field is not an easy task. Where the enclosure has a size that is resonant at the frequency of operation, it can be easier to generate a robust EM field since a resonant standing wave may be generated within the enclosure. However, in the RFID field the usable frequencies of operation are strictly controlled and are limited. It has been found that enclosures are desired for the storage of certain articles that do not have a resonant frequency that matches one of the allowed RFID frequencies. Thus, a robust EM field must be established in another way.

Additionally, where EM energy is introduced to such an enclosure for reading the RFID tags within, efficient energy transfer is of importance. Under static conditions, the input or injection of EM energy into an enclosure can be maximized with a simple impedance matching circuit positioned between the conductor delivering the energy and the enclosure. As is well known to those of skill in the art, such impedance matching circuits or devices maximize the power transfer to the enclosure while minimizing the reflections of power from the enclosure. Where the enclosure impedance changes due to the introduction or removal of articles to or from the enclosure, a static impedance matching circuit may not provide optimum energy transfer into the enclosure. If the energy transfer and resulting RF field intensity within the enclosure were to fall below a threshold level, some or many of the tags on articles within the enclosure would not be activated to identify themselves, leaving an ineffective inventory system.

It is a goal of many health care facilities to keep the use of EM energy to a minimum, or at least contained. The use of high-power readers to locate and extract data from RFID tags is generally undesirable in health care facilities, although it may be acceptable in warehouses that are sparsely populated with workers, or in aircraft cargo holds. Radiating a broad beam of EM energy at a large area, where that EM energy may stray into adjacent, more sensitive areas, is undesirable. Efficiency in operating a reader to obtain the needed identification information from tags is an objective. In many cases where RFID tags are read, handheld readers are used. Such readers transmit a relatively wide beam of energy to reach all RFID tags in a particular location. While the end result of activating each tag and reading it may be accomplished, the transmission of the energy is not controlled except by the aim of the user. Additionally, this is a manual system that will require the services of one or more individuals, which can also be undesirable in facilities where staff is limited. In many such systems, the RFID reader is a portable unit with a "tethered reader head" thereby imposing the extra time and effort to find the unit, be sure it is powered, take it to the medication cabinet where the inventory is required, open the cabinet, collect the inventory data, and then upload the inventory data to a pharmacy server. All of the foregoing take significant amounts of time.

Hence, those of skill in the art have recognized a need for a means to provide a more automated inventory management system, which is installed into a drawer or drawers of a medication cabinet that can automatically upload inventory data regarding the contents of a selected container, such as a drawer, without requiring the manual efforts of a facility's personnel. A need has also been recognized for an RFID tag reader system in which the efficient use of energy is made to activate and read all RFID tags in an enclosed area. A further need for establishing a robust EM field in enclosures to activate and read tags disposed at random orientations has also been recognized. A further need has been recognized for an automated system to identify articles stored in a metal cabinet without the need to gain access to the cabinet. Yet another need has been recognized for energizing containers, such as drawers at non-resonant frequencies sufficient to read RFID tags in those containers. A further recognized need is to RFID-enable existing medication cabinets or other storage containers. The present invention fulfills these needs and others.

SUMMARY OF THE INVENTION

Briefly and in general terms, the present invention is directed to a self-contained RF module system for establishing an electromagnetic field in a preexisting non-resonant container, such as a drawer, to energize the container with sufficient field strength to read RFID tags located in that container, so that tagged medical articles may be identified and tracked. The system and method in accordance with the invention are particularly suited to installation into medication cabinets that do not have automatic identification systems for their contents.

In one aspect there is provided an RF-enabling module system for establishing an RF field within a container having a predetermined size in which items are placed, the RF-enabling module system comprising a base having a mounting fixture configured to mount the base in a selected location in relation to a container in which items are placed, the container having a container size and the base having a base size selected to be compatible with the container size so that the base and components thereof may interact with items placed within the container, a tunable probe antenna located on the base and configured to establish a robust activating RF field within the container within a predetermined frequency range regardless of a resonant frequency of the container, wherein the robust RF field covers all items placed in the container, a receiving antenna located on the base and configured to receive data signals produced within the container in response to the activating RF field, a reader unit located on the base configured to receive the data signals from the receiving antenna, and process the data signals, and a communications unit located on the base configured to receive the processed data signals from the reader unit and communicate the processed data signals to a remote location.

More detailed aspects in accordance with the invention include the module system further comprising a Faraday cage formed substantially completely around the items in the container wherein at least the probe antenna and the receiving antenna are located within the Faraday cage. The probe antenna is configured to automatically retune itself to establish the robust activating RF field within the container to accommodate more or fewer items in the container. The container has a resonant frequency and the predetermined frequency range of the probe antenna does not include the resonant frequency Other aspects include the RF-enabling module system further comprising a switch between the reader and the probe antenna and the receiving antenna with the reader configured to switch each antenna on or off for purposes of activating the container and receiving data from the container. The size of the base is selected so that the base will be compatible to fit with the size of a preexisting container, whereby the module system is used to retrofit the preexisting container. The size of the base is selected so that the base will be compatible to fit with the size of a container being constructed, whereby the module system is used to form an integrated part of the container being constructed.

More detailed aspects include the antennae being located on top of respective mesa structures that are formed on the base. Multiple probe antennae and multiple receiving antennae are used and wherein the reader is centrally located on the base between the multiple antennae. Four receiving antennae, two probe antennae, two switches, and the reader comprises an RFID reader circuit board mounted to the base, the probe antennae, the switches, and the reader being mounted to an RFID reader circuit board with the reader circuit board is centrally located between the antennae.

Other aspects include an RFID-enabling module system for establishing an RF field within a container having a predetermined size in which items are placed, the RFID-enabling module system comprising a base having a mounting fixture configured to mount the base in a selected location in relation to a container in which items are placed, each item having an RFID tag with a unique data identification, the container having a container size and the base having a base size selected to be compatible with the container size so that the base and components thereof may interact with tagged items placed within the container, a tunable probe antenna located on the base and configured to establish a robust activating RF field within the container within a predetermined frequency range that does not include a resonant frequency of the container, the robust RF field selected to activate the RFID tags of the items placed in the container, a receiving antenna located on the base and configured to receive RFID data signals produced within the container in response to the activating RF field, an RFID reader unit located on the base configured to receive the RFID data signals from the receiving antenna, and process the data signals, and a communications unit located on the base configured to receive the processed data signals from the reader unit and communicate the processed data signals to a remote location, a Faraday cage formed substantially completely around the tagged items in the container, wherein at least the probe antenna and the receiving antenna are located within the Faraday cage, a data base located at the remote location, the data base containing information pertaining to the tagged items that is correlated with the data identifications of the tags respectively attached to the items, and a remote processor located at the remote location configured receive the processed data signals, compare them to the data base, and provide information relating to the tagged items based on the comparison.

Further detailed aspects include the RFID-enabling module system wherein the information relating to the tagged items based on the comparison includes at least one of:
 inventory level compared against minimum/maximum levels for reordering;
 counterfeit prevention;
 ePedigree/serialization capability;
 lot control;
 medication error prevention;
 NDC control; and
 expiration control.

Additionally, the reader is configured to automatically establish the RF field automatically in the container according to a schedule. The probe antenna is configured to automatically retune itself to establish the robust activating RF field within the container to accommodate more or fewer items in the container.

In accordance with method aspects of the invention, there is provided a method for RFID-enabling a container to establish an RF field within the container, the container having a predetermined size in which RFID tagged items are placed, the method comprising mounting a base in a selected location in relation to a container in which RFID tagged items are placed, the container having a container size and the base having a base size selected to be compatible with the container size so that the base and components thereof may interact with the RFID tags on the items placed within the container, exciting a tunable probe antenna mounted to the base to establish a robust RFID activating RF field within the container within a predetermined frequency range regardless of a resonant frequency of the container, the robust RF field covering all RFID tagged items placed in the container, receiving unique RFID identification data signals from RFID tags on items in the container after they have been activated by the RF field, reading and processing the RFID data signals from the activated items in the container, and communicating the processed RFID data signals to a remote location.

More detailed method aspects include forming a Faraday cage substantially completely around the RFID tagged items in the container and mounting at least the probe antenna and the receiving antenna within the Faraday cage. Further, the method comprises automatically retuning the probe antenna to establish the robust RFID activating RF field within the container to accommodate more or fewer RFID tagged items in the container. Additionally, the step of exciting includes the step of exciting the tunable probe antenna with a frequency range that does not include a resonant frequency of the container.

The features and advantages of the invention will be more readily understood from the following detailed description that should be read in conjunction with the accompanying drawings.

BRIEF DESCRIPTION OF THE DRAWINGS

FIG. 3 is a block and flow diagram showing an embodiment in which an RFID reader transmits activating EM energy into a drawer containing RFID tags with a single transmitting antenna, receives the data output from the activated RFID tags with a single receiving antenna, a computer controlling the transmission of activating energy and receiving the data from the activated RFID tags for processing;

FIG. 4 is a block and flow diagram similar to FIG. 3 showing an embodiment in which an RFID reader transmits activating EM energy into a drawer containing RFID tags with two transmitting antennae, receives the data output from the activated RFID tags with three receiving antennae, and as in FIG. 3, a computer controlling the transmission of activating energy and receiving the data from the activated RFID tags for processing;

FIG. 11 shows a probe, a connector, and a passive matching circuit that is used to improve the impedance match between the probe and enclosure;

FIG. 12 shows an active matching circuit connected between a probe located in an enclosure and a transceiver, the active matching circuit comprising a tunable capacitor, a dual-directional coupler, multiple power sensors, and a comparator used to provide a closed-loop, variable matching circuit to improve the impedance match between the probe and the enclosure;

FIG. 23 shows a medication administration cabinet having a control unit, a display, which in one embodiment comprises a touch screen for the input of data and instructions, a pointing device in the form of a mouse, a plurality of drawers used for storing medications having RFID tags, and connections to a server, a data base, and a cart;

DETAILED DESCRIPTION OF THE PREFERRED EMBODIMENTS

Figure 1:
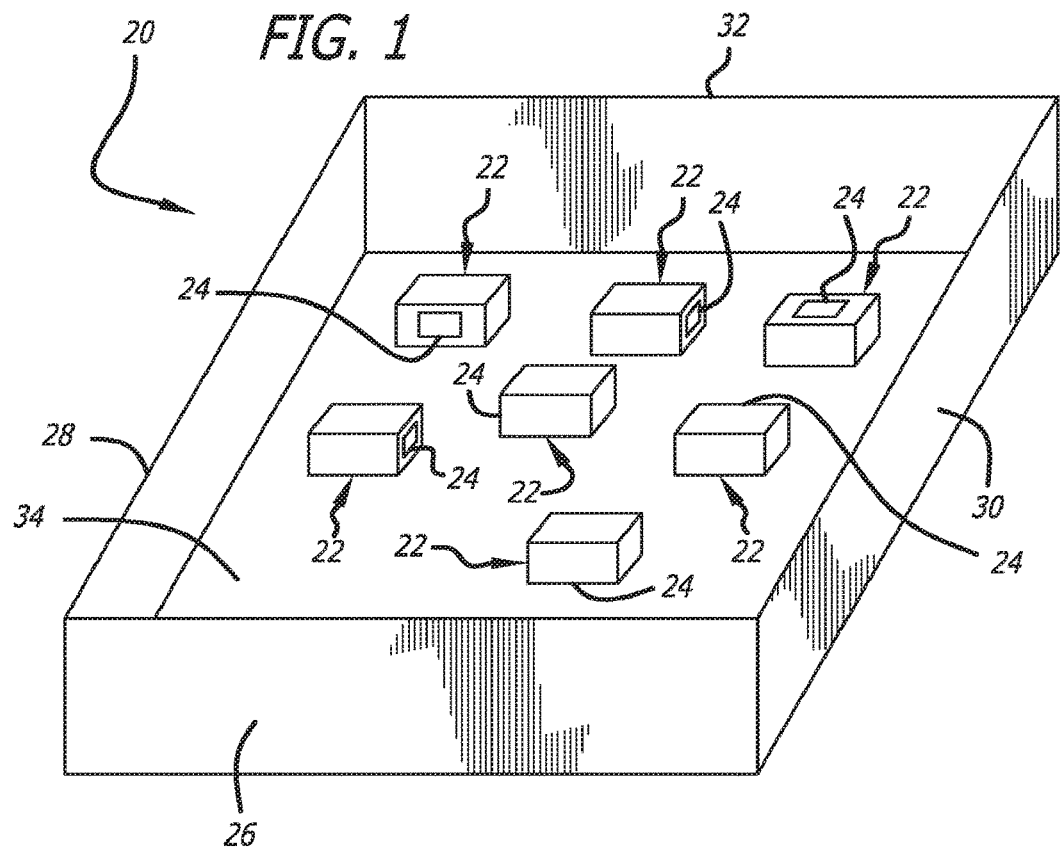
FIG. 1 is a schematic diagram of a drawer that may be positioned within a medical dispensing cabinet, showing the storage of a plurality of medical articles randomly positioned in the drawer, each of those articles having an integral RFID tag oriented randomly.

Referring now in more detail to the exemplary drawings for purposes of illustrating embodiments of the invention, wherein like reference numerals designate corresponding or like elements among the several views, there is shown in FIG. 1 a schematic representation of a partial enclosure 20 in which a plurality of medical articles 22 are stored, each with a respective RFID tag 24 that has a unique identification number. The partial enclosure may comprise a drawer having a front 26, a left side 28, a right side 30, a rear 32, and a bottom 34. These articles are randomly distributed in the drawer with the RFID tags facing in various and random directions.

As used in regard to the embodiments herein, "reader" and "interrogator" refer to a device that may read or write/read. The data capture device is always referred to as a reader or an interrogator regardless of whether it can only read or is also capable of writing. A reader typically contains a radio frequency module (a transmitter and a receiver, sometimes referred to as a "transceiver"), a control unit and a coupling element (such as an antenna or antennae) to the RFID tag. Additionally, many readers include an interface for forwarding data elsewhere, such as an RS-232 interface. The reader, when transmitting, has an interrogation zone within which an RFID tag will be activated. When within the interrogation zone, the RFID tag will draw its power from the electrical/magnetic field created in the interrogation zone by the reader. In a sequential RFID system (SEQ), the interrogation field is switched off at regular intervals. The RFID tag is programmed to recognize these "off" gaps and they are used by the tag to send data, such as the tag's unique identification number. In some systems, the tag's data record contains a unique serial number that is incorporated when the tag is manufactured and which cannot be changed. This number may be associated in a data base with a particular article when the tag is attached to that article. Thus, determining the location of the tag will then result in determining the location of the article to which it is attached. In other systems, the RFID tag may contain more information about the article to which it is attached, such as the name or identification of the article, its expiration date, it dose, the patient name, and other information. The RFID tag may also be writable so that it can be updated.

As used in regard to the embodiments herein, "tag" is meant to refer to an RFID transponder. Such tags typically have a coupling element, such as an antenna, and an electronic microchip. The microchip includes data storage, also referred to as memory.

Figure 2:
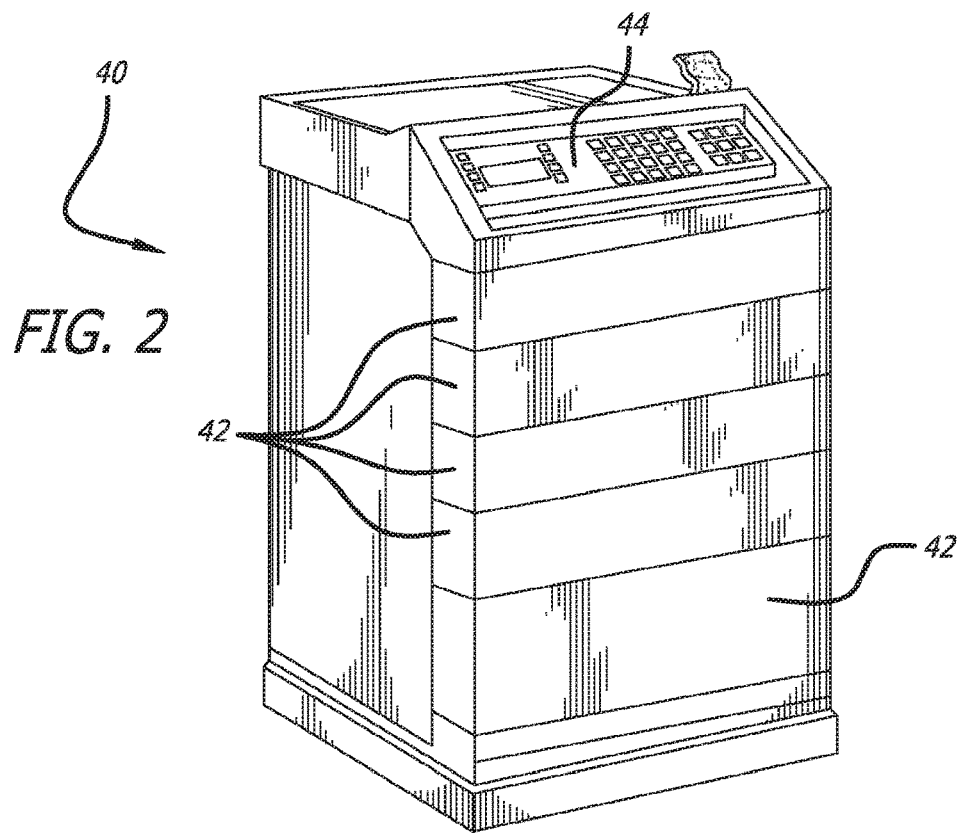
FIG. 2 is a perspective view of a medication dispensing cabinet having five drawers, one of which is similar to the schematic view of FIG. 1, the cabinet also having an integral computer for controlling access to the cabinet and performing inventory tracking by periodically reading any RFID tags placed on articles stored within the cabinet, and for reporting the identified articles to a remote computer.

FIG. 2 presents a representative medical dispensing cabinet 40 comprising a plurality of movable drawers 42. In this embodiment, there are five drawers that slide outwardly from the cabinet so that access is provided to the contents of the drawers. FIG. 1 is a schematic diagram of a representative drawer that may be positioned within the cabinet of FIG. 2 for sliding outward to provide access to the drawer's contents and for sliding inward into the cabinet to secure the drawer's contents. The cabinet also comprises an integral computer 44 that may be used to control access to the drawers and to generate data concerning access and contents, and to communicate with other systems. In this embodiment, the computer generates data concerning the number and type of articles in the drawers, the names of the patients for whom they have been prescribed, the prescribed medications and their prescribed administration dates and times, as well as other information. In a simpler system, the computer may simply receive unique identification numbers from stored articles and pass those identification numbers to an inventory control computer that has access to a data base for matching the identification numbers to article descriptions.

Such a cabinet may be located at a nursing station on a particular floor of a health care institution and may contain the prescriptions for the patients of that floor. As prescriptions are prepared for the patients of that floor, they are delivered and placed into the cabinet 40. They are logged into the integral computer 44, which may notify the pharmacy of their receipt. A drawer may also contain non-prescription medical supplies or articles for dispensing to the patients as determined by the nursing staff. At the appropriate time, a nurse would access the drawer in which the medical articles are stored through the use of the computer 44, remove a particular patient's prescriptions and any needed non-prescription articles, and then close the drawer so that it is secured. In order to access the cabinet, the nurse may need to provide various information and may need a secure access code. The drawers 42 may be locked or unlocked as conditions require.

The computer 44 in some cases may be in communication with other facilities of the institution. For example, the computer 44 may notify the pharmacy of the health care institution that a patient's prescription has been removed from the cabinet for administration at a particular day and time. The computer may also notify the finance department of the health care institution of the removal of prescriptions and other medical articles for administration to a particular patient. This medication may then be applied to the patient's account. Further, the computer 44 may communicate to administration for the purpose of updating a patient's Medication Administration Record (MAR), or e-MAR. The medication cabinet 40 computer 44 may be wirelessly connected to other computers of the health care institution or may have a wired connection. The cabinet may be mounted on wheels and may be moved about as needed or may be stationary and unable to move.

Systems that use RFID tags often employ an RFID reader in communication with one or more host computing systems that act as depositories to store, process, and share data collected by the RFID reader. Turning now to FIGS. 3 and 4, a system and method 50 for tracking articles are shown in which a drawer 20 of the cabinet 40 of FIG. 2 is monitored to obtain data from RFID tags disposed with articles in that drawer. As mentioned above, a robust field of EM energy needs to be established in the storage site so that the RFID tags mounted to the various stored articles will be activated, regardless of their orientation.

In FIGS. 3 and 4, the tracking system 50 is shown for identifying articles in an enclosure and comprises a transmitter 52 of EM energy as part of an RFID reader. The transmitter 52 has a particular frequency, such as 915 MHz, for transmitting EM energy into a drawer 20 by means of a transmitting antenna 54. The transmitter 52 is configured to transmit the necessary RFID EM energy and any necessary timing pulses and data into the enclosure 20 in which the RFID tags are disposed. In this case, the enclosure is a drawer 20. The computer 44 of an RFID reader 51 controls the EM transmitter 52 to cycle between a transmit period and a non-transmit, or off, period. During the transmit period, the transmitted EM energy at or above a threshold intensity level surrounds the RFID tags in the drawer thereby activating them. The transmitter 52 is then switched to the off period during which the RFID tags respond with their respective stored data.

The embodiment of FIG. 3 comprises a single transmitting probe antenna 54 and a single receiving antenna 56 oriented in such a manner so as to optimally read the data transmitted by the activated RFID tags located inside the drawer 20. The single receiving antenna 56 is communicatively coupled to the computer 44 of the reader 50 located on the outside of the drawer 20 or on the inner bottom of the drawer. Other mounting locations are possible. Coaxial cables 58 or other suitable signal links can be used to couple the receiving antenna 56 to the computer 44. A wireless link may be used in a different embodiment. Although not shown in the figures, those skilled in the art will recognize that various additional circuits and devices are used to separate the digital data from the RF energy, for use by the computer. Such circuits and devices have not been shown in FIGS. 3 and 4 to avoid unneeded complexity in the drawing.

The embodiment of FIG. 4 is similar to the embodiment of FIG. 3 but instead uses two transmitting probe antennae 60 and 62 and three receiving antennae 64, 66, and 68. The configuration and the number of transmitting probe antennae and receiving antennae to be used for a system may vary based at least in part on the size of the enclosure 20, the frequency of operation, the relationship between the operation frequency and the natural resonance frequency of the enclosure, and the expected number of RFID tags to be placed in it, so that all of the RFID tags inside the enclosure can be reliably activated and read. The location and number of RFID reader components can be dependent on the particular application. For example, fewer components may be required for enclosures having a relatively small size, while additional components, such as shown in FIG. 4, may be needed for larger enclosures. Although shown in block form in FIGS. 3 and 4, it should be recognized that each receiving antenna 56, 64, 66, and 68 of the system 50 may comprise a sub-array in a different embodiment.

The transmit antennae (54, 60, and 62) and the receive antennae (56, 64, 66, and 68) may take different forms. In one embodiment as is discussed in more detail below, a plurality of "patch" or microstrip antennae were used as the reader receiving antennae and were located at positions adjacent various portions of the bottom of the drawer while the transmit antennae were wire probes located at positions adjacent portions of the top of the drawer. It should be noted that in the embodiments of FIGS. 3 and 4, the RFID reader 50 may be permanently mounted in the same cabinet at a strategic position in relation to the drawer 20.

One solution for reliably interrogating densely packed or randomly oriented RFID tags in an enclosure is to treat the enclosure as a resonant cavity. Establishing a resonance within the cavity enclosure can result in a robust electromagnetic field capable of activating all RFID tags in the enclosure. This can be performed by building an enclosure out of electrically conductive walls and exciting the metallic enclosure, or cavity, using a probe or probes to excite transverse electric (TE) or transverse magnetic (TM) fields in the cavity at the natural frequency of resonance of the cavity. This technique will work if the cavity dimensions can be specifically chosen to set up the resonance at the frequency of operation or if the frequency of operation can be chosen for the specific enclosure size. Since there are limited frequency bands available for use in RFID applications, varying the RFID frequency is not an option for many applications. Conversely, requiring a specific set of physical dimensions for the enclosure so that the natural resonant frequency of the enclosure will equal the available RFID tag activating frequency will restrict the use of this technique for applications where the enclosure needs to be of a specific size. This latter approach is not practical in view of the many different sizes, shapes, and quantities of medical articles that must be stored.

Figure 5:
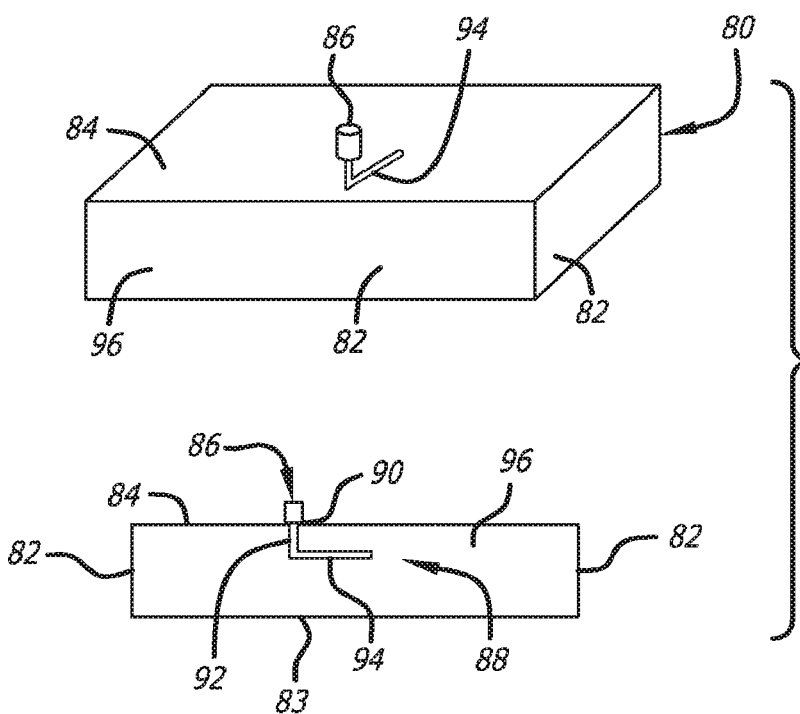
FIG. 5 shows an enclosure with a single probe and a connector, the probe being configured to inject EM energy into the enclosure and excite a TE mode.

Referring now to FIG. 5, a rectangular enclosure 80 is provided that may be formed as part of a medical cabinet, such as the cabinet shown in FIG. 2. It may be embodied as a frame disposed about a non-metallic drawer in such a cabinet. The enclosure 80 is formed of metallic or metallized walls 82, floor 83, and ceiling 84 surfaces, all of which are electrically conductive. All of the walls 82, floor 83, and ceiling 84 may also be referred to herein as "walls" of the enclosure. FIG. 5 also shows the use of an energy coupling or probe 86 located at the top surface 84 of the enclosure 80. In this embodiment, the probe takes the form of a capacitor probe 88 in that the probe 88 has a first portion 94 that proceeds axially through a hole 90 in the ceiling 84 of the enclosure. The purpose of the coupling is to efficiently transfer the energy from the source 52 (see FIGS. 3 and 4) to the interior 96 of the enclosure 80. The size and the position of the probe are selected for effective coupling and the probe is placed in a region of maximum field intensity. In FIG. 5, a $TE_{01}$ mode is established through the use of capacitive coupling. The length and distance of the bent portion 94 of the probe 88 affects the potential difference between the probe and the enclosure 80.

Figure 6:
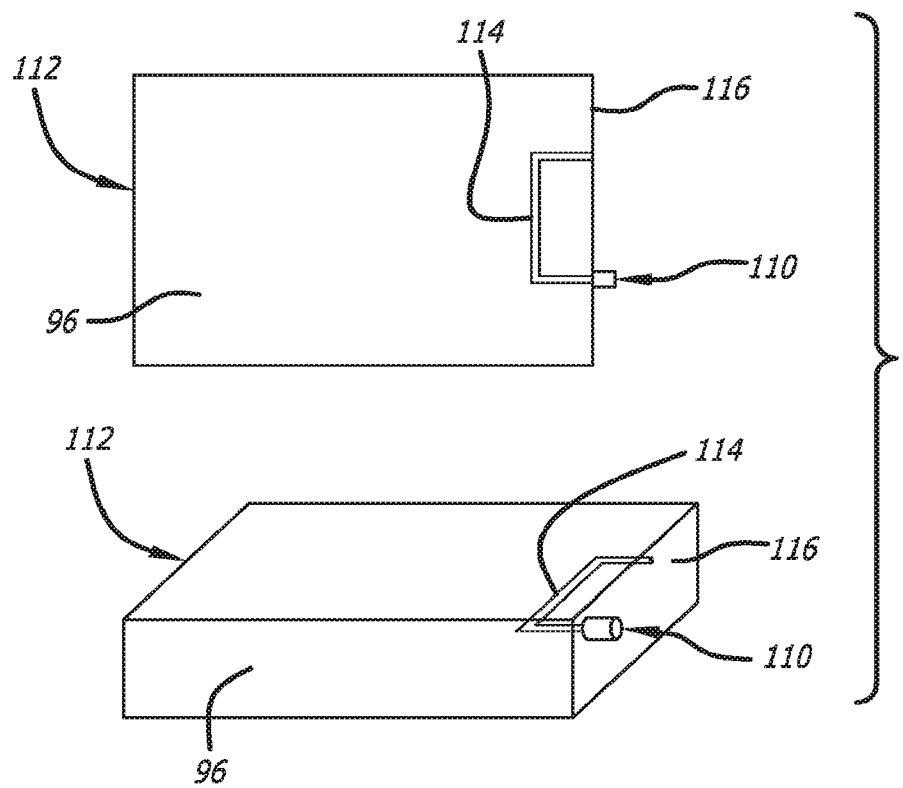
FIG. 6 shows an enclosure with a single probe and a connector, the probe being configured to inject EM energy into the enclosure and excite a TM mode.

Similarly, FIG. 6 presents an inductive coupling 110 of the external energy to an enclosure 112. The coupling takes the form of a loop probe 114 mounted through a side wall 116 of the enclosure. The purpose of this probe is to establish a $TM_{01}$ mode in the enclosure.

Figure 7:
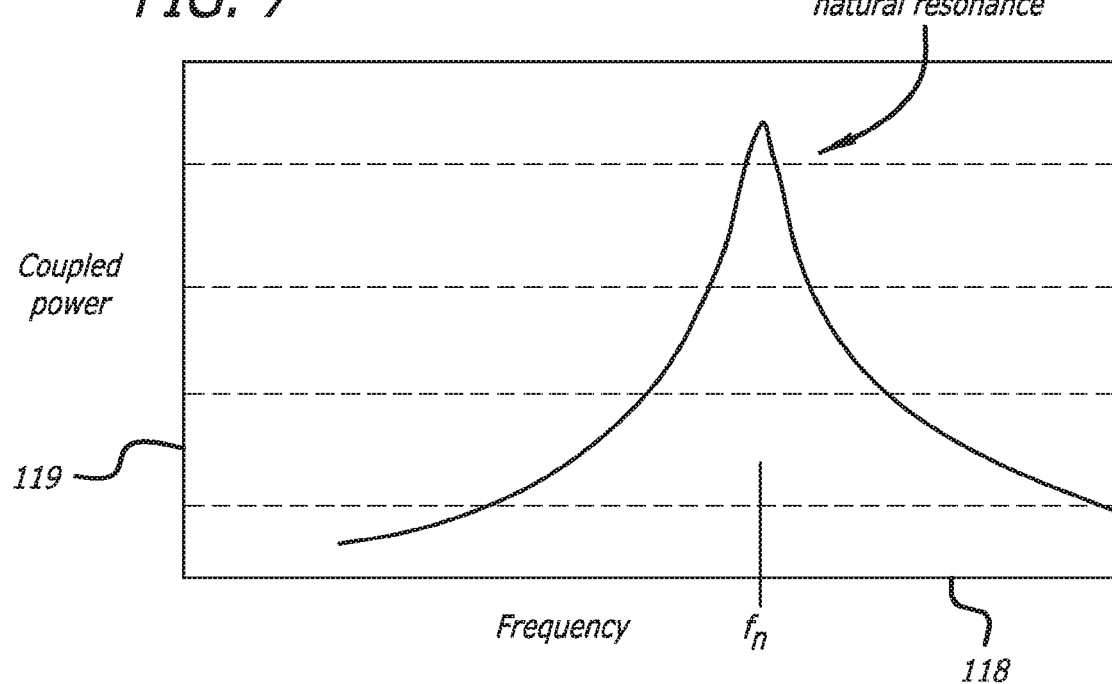
FIG. 7 shows a plot of coupled power in an enclosure as a function of frequency for a resonant enclosure where $f_n$ is the natural resonance frequency of the enclosure.

The rectangular enclosures 80 and 112 shown in FIGS. 5 and 6 each have a natural frequency of resonance $f_n$, shown in FIG. 7 and indicated on the abscissa axis 118 of the graph by $f_n$. This is the frequency at which the coupled power in the enclosure is the highest, as shown on the ordinate axis 119 of the graph. If the injected energy to the enclosure does not match the $f_n$ frequency, the coupled power will not benefit from the resonance phenomenon of the enclosure. In cases where the frequency of operation cannot be changed, and is other than $f_n$, and the size of the enclosure cannot be changed to obtain an $f_n$ that is equal to the operating frequency, another power coupling apparatus and method must be used. In accordance with aspects of the invention, an apparatus and method are provided to result in a forced resonance $f_f$ within the enclosure to obtain a standing wave within the enclosure with constructive interference. Such a standing wave will establish a robust energy field within the enclosure strong enough to activate all RFID tags residing therein.

Figure 8:
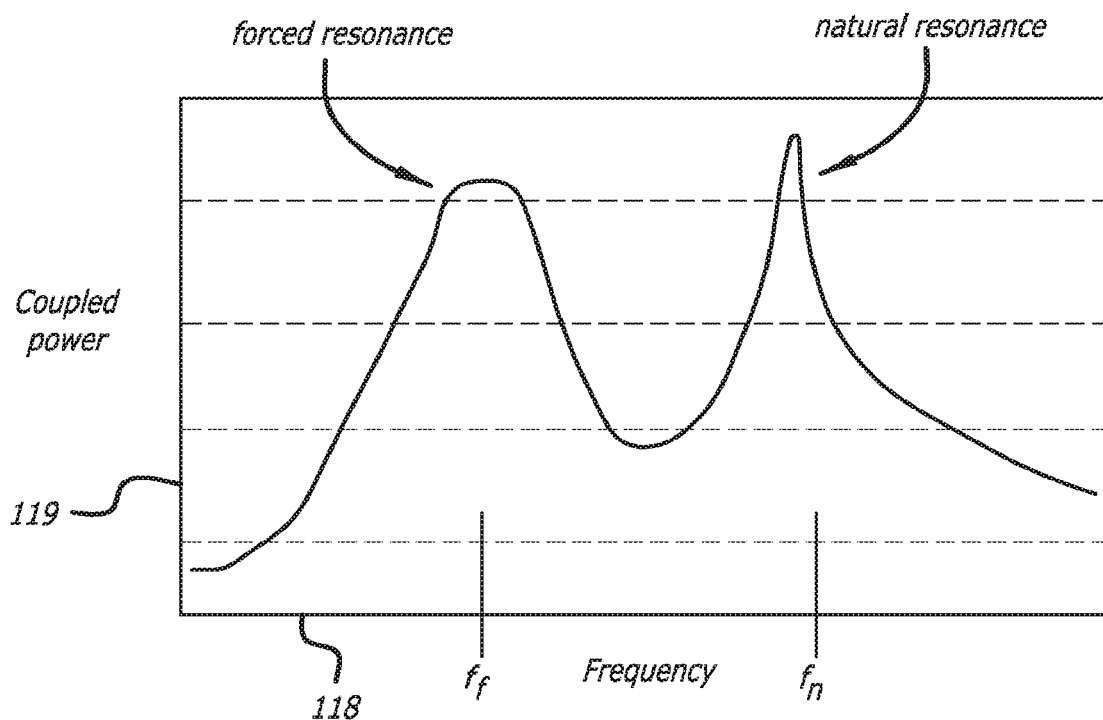
FIG. 8 shows a plot of coupled power (ordinate axis) in an enclosure as a function of frequency (abscissa axis), where $f_f$ is a forced resonance frequency, or otherwise referred to as a frequency that is not equal to the resonant frequency of the enclosure, and $f_n$ is the natural resonant frequency of the enclosure, showing the establishment of a robust field of coupled power in the enclosure at the $f_f$ frequency.

When an EM wave that is resonant with the enclosure enters, it bounces back and forth within the enclosure with low loss. As more wave energy enters the enclosure, it combines with and reinforces the standing wave, increasing its intensity (constructive interference). Resonation occurs at a specific frequency because the dimensions of the cavity are an integral multiple of the wavelength at the resonance frequency. In the present case where the injected energy is not at the natural resonance frequency $f_n$ of the enclosure, a solution in accordance with aspects of the invention is to set up a "forced resonance" in an enclosure. This forced resonance is different from the natural resonance of the enclosure in that the physical dimensions of the enclosure are not equal to an integral multiple of the wavelength of the excitation energy, as is the case with a resonant cavity. A forced resonance can be achieved by determining a probe position, along with the probe length to allow for energy to be injected into the cavity such that constructive interference results and a standing wave is established. The energy injected into the enclosure in this case will set up an oscillatory field region within the cavity, but will be different from a standing wave that would be present at the natural resonance frequency $f_n$ of a resonant cavity. The EM field excited from this forced resonance will be different than the field structure found at the natural resonance of a resonant cavity, but with proper probe placement of a probe, a robust EM field can nevertheless be established in an enclosure for RFID tag interrogation. Such is shown in FIG. 8 where it will be noted that the curve for the forced resonance $f_f$ coupled power is close to that of the natural resonance $f_n$.

Figure 9:
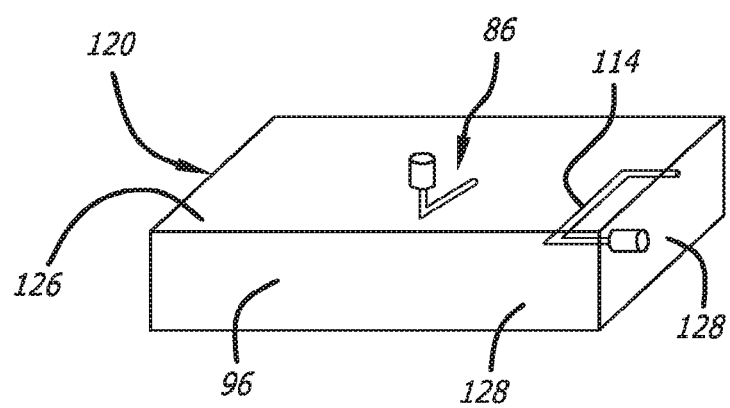
FIG. 9 shows an enclosure with two probes each with a connector for injecting EM energy into the enclosure, one probe being a TM probe and the other being a TE probe.

Turning now to FIG. 9, an enclosure 120 having two energy injection probes is provided. The first probe 86 is capacitively coupled to the enclosure 120 in accordance with FIG. 5 to establish a $TE_{01}$ mode. The second probe 114 is inductively coupled to the enclosure 120 in accordance with FIG. 6 to establish a $TM_{01}$ mode. These two probes are both coupled to the enclosure to inject energy at a frequency $f_f$ that is other than the natural resonance frequency $f_n$ of the enclosure. The placement of these probes in relation to the ceiling 126 and walls 128 of the enclosure will result in a forced resonance within the enclosure 120 that optimally couples the energy to the enclosure and establishes a robust EM field within the enclosure for reading RFID tags that may be located therein. The placement of these probes in relation to the walls of the enclosure, in accordance with aspects of the invention, result in the forced resonance curve $f_f$ shown in FIG. 8.

Figure 10:
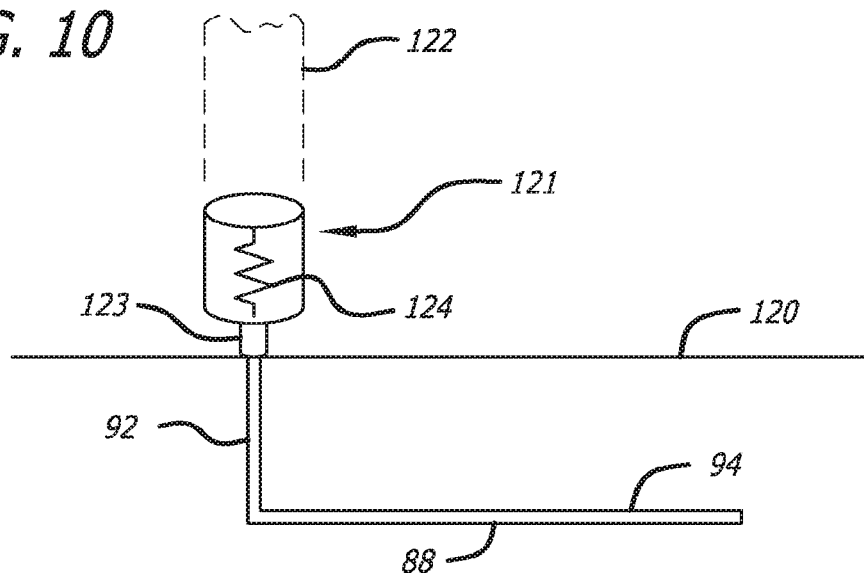
FIG. 10 shows a probe, a connector, and an attenuator that is used to improve the impedance match between the probe and the enclosure.

Referring briefly to FIG. 10, an impedance matching circuit 121 is shown that functions to match the impedance of a source of energy 122 to the enclosure 120. The impedance matching circuit is located between the coaxial cable 122 that feeds activating energy to the enclosure 120 and the capacitively coupled probe 88 through a hole in the metallic ceiling 126 of the enclosure. While the hole is not shown in the drawing of FIG. 10, the insulator 123 that electrically insulates the probe from the metallic ceiling is shown. In this case, the matching circuit 121 consists of only a resistive attenuator 124 used to reduce reflections of energy by the enclosure 120. However, as will be appreciated by those of skill in the art, capacitive and inductive components are likely to exist in the enclosure and in the coupling 88. FIG. 11 on the other hand presents an impedance matching circuit 124 having passive reactive components for use in matching the impedance of the coaxial cable/energy source 122 and the enclosure 120. In this exemplary impedance matching circuit 124, an inductive component 125 and a capacitive component 127 are connected in series, although other configurations, including the addition of a resistive component and other connection configurations are possible.

Passive components such as resistors, inductors, and capacitors shown in FIGS. 10 and 11 can be used to form matching circuits to match the impedances of the energy source and the enclosure. This will aid in coupling power into the enclosure. However, the passive matching circuit will improve the impedance match for a specific enclosure loading, such as an empty enclosure, partially loaded, or fully loaded enclosure. However, as the enclosure contents are varied, the impedance match may not be optimized due to the variation in contents in the enclosure causing the impedance properties of the enclosure to change.

This non-optimal impedance match caused by variation in enclosure loading can be overcome by the use of an active impedance matching circuit which utilizes a closed loop sensing circuit to monitor forward and reflected power. Referring now to FIG. 12, an active matching circuit 130 is provided that comprises one or several fixed value passive components such as inductors 132, capacitors 134, or resistors (not shown). In addition, one or several variable reactance devices, such as a tunable capacitor 134, are incorporated into the circuit; these tunable devices making this an active impedance matching circuit. The tunable capacitor 134 can take the form of a varactor diode, switched capacitor assembly, MEMS capacitor, or BST (Barium Strontium Titanate) capacitor. A control voltage is applied to the tunable capacitor 134 and varied to vary the capacitance provide by the device. The tunable capacitor 134 provides the capability to actively change the impedance match between the probe 140 and the enclosure 142.

To complete the active matching circuit, a dual directional coupler 144 along with two power sensors 146 can be incorporated. The dual directional coupler 144 and the power sensors 146 provide the ability to sense forward and reflected power between the RFID transceiver 148 and the active matching circuit 130 and enclosure 142. Continuous monitoring of the ratio of forward and reflected power by a comparator 150 provides a metric to use to adjust the tunable capacitor 134 to keep the probe 140 impedance matched to the enclosure 142. An ability to continuously monitor and improve the impedance match as the contents of the enclosure are varied is provided with the active matching circuit 130.

Figure 13:
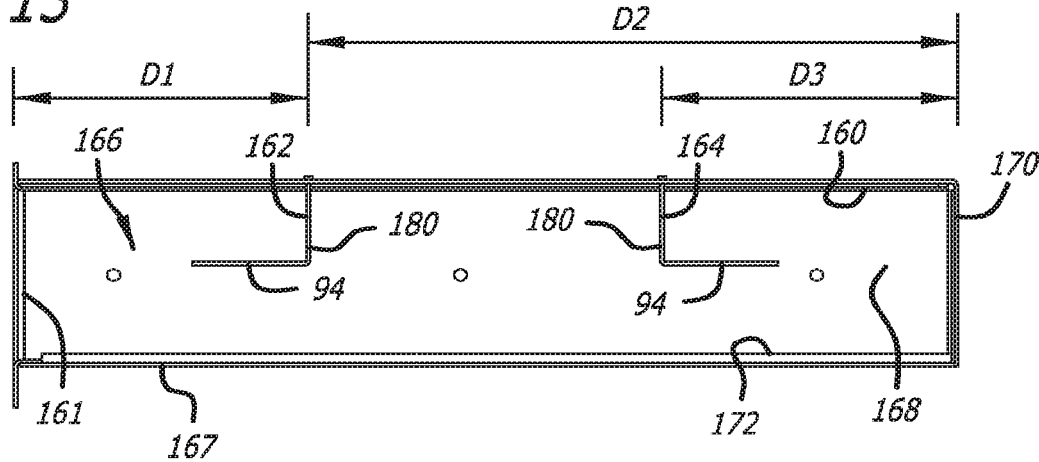
FIG. 13 provides a side cross-sectional view of the cabinet of FIG. 2 at the location of a drawer with the drawer removed for clarity, showing the placement of two probe antennae in a "ceiling mount" configuration for establishing a robust EM field in the drawer when it is in place in the cabinet in the closed position.

Referring now to the side cross-sectional view of FIG. 13, two ceiling-mounted 160 probe antennae 162 and 164 are shown mounted within an enclosure, which may also be referred to herein as a cavity 166, which in this embodiment, operates as a Faraday cage. As shown, the Faraday cage 166 comprises walls (one of which is shown) 168, a back 170, a floor 172, a ceiling 160, and a front 161 (only the position of the front wall is shown). All surfaces forming the cavity are electrically conductive, are electrically connected with one another, and are structurally formed to be able to conduct the frequency of energy $f_f$ injected by the two probes 162 and 164. In this embodiment, the cavity 166 is constructed as a metal frame 167 that may form a part of a medical supply cabinet similar to that shown in FIG. 2. Into that metal frame may be mounted a slidable drawer. The slidable drawer in this embodiment is formed of electrically inert material, that is, it is not electrically conductive, except for the front. When the drawer is slid into the cabinet to a closed configuration, the electrically conductive front panel of the drawer comes into electrical contact with another part or parts of the metallic frame 167 thereby forming the front wall 161 of the Faraday cage 167.

The amount of penetration or retention into the cavity by the central conductor 180 of each probe is selected so as to achieve optimum coupling. The length of the bent portion 94 of the probe is selected to result in better impedance matching. The position of the probe in relation to the walls of the cavity is selected to create a standing wave in the cavity. In this embodiment, the probe antennae 162 and 164 have been located at a particular distance D1 and D3 from respective front 161 and back 170 walls. These probe antennae, in accordance with one aspect of the invention, are only activated sequentially after the other probe has become inactivated. It has been found that this configuration results in a standing wave where the injected energy waves are in phase so that constructive interference results.

Figure 14:
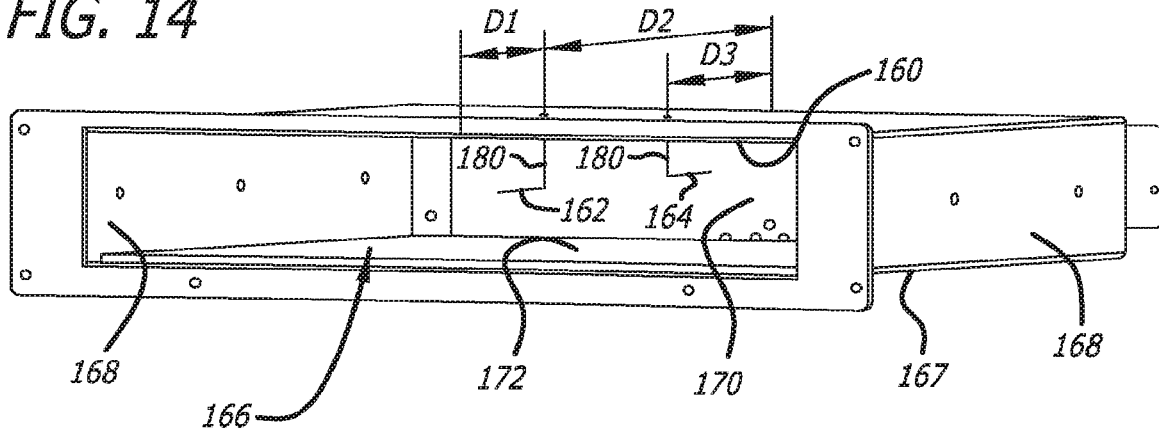
FIG. 14 is a perspective view of the metallic enclosure showing the probe configuration of FIG. 13 again showing the two probe antennae for establishing a robust EM field in a drawer to be inserted.

FIG. 14 is a front perspective view of the probe configuration of FIG. 13 again showing the two probe antennae 162 and 164 located in a Faraday-type enclosure 166 for establishing a robust EM field in an article storage drawer to be inserted. It should be noted again that the Faraday cavity 166 is constructed as a metallic frame 167. In this figure, the cavity is incomplete in that the front surface of the "cage" is missing. In one embodiment, this front surface is provided by an electrically conductive front panel of a slidable drawer. When the drawer is slid into the cabinet, the front panel will make electrical contact with the other portions of the metallic frame 167 thereby completing the Faraday cage 166, although other portions of the drawer are plastic or are otherwise non-electrically conductive. In the embodiment discussed and shown herein, the two probe antennae 162 and 164 are both located along a centerline between the side walls 166 and 168 of the frame 166. The enclosure in one embodiment was 19.2 inches wide with the probe antennae spaced 9.6 inches from each side wall. This centered location between the two side walls was for convenience in the case of one embodiment. The probes may be placed elsewhere in another embodiment. In this embodiment, the spacing of the probes 162 and 164 from each other is of little significance since they are sequentially activated. Although not shown, two receiving antennae will also be placed into the Faraday cage 166 to receive response signals from the activated RFID tags residing within the cavity 166.

It will also be noted from reference to the figures that the probes each have a bent portion used for capacitive coupling with the ceiling 160 of the cavity, as is shown in FIG. 13. The front probe 162 is bent forward while the back probe 164 is bent rearward A purpose for this configuration was to obtain more spatial diversity and obtain better coverage by the EM field established in the drawer. Other arrangements may be possible to achieve a robust field within the cavity 166. Additionally two probes were used in the particular enclosure 166 so that better EM field coverage of the enclosure 166 would result.

Figure 15:
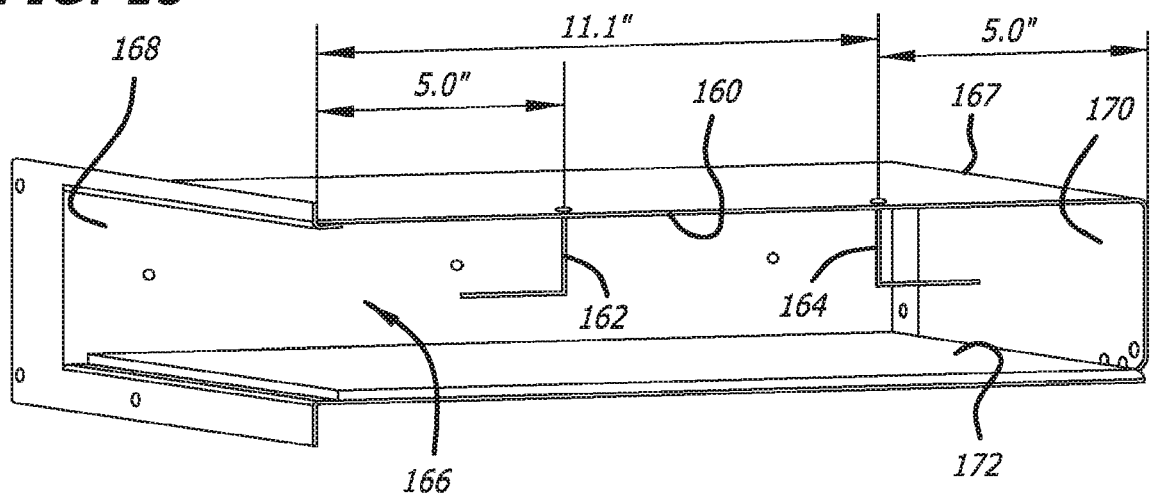
FIG. 15 is a cutaway perspective side view of the metallic enclosure or frame in which are mounted the dual probe antennae of FIGS. 13 and 14 with the drawer removed for clarity.

FIG. 15 is a cutaway perspective side view of the dual probe antennae 162 and 164 of FIGS. 13 and 14, also with the drawer removed for clarity. The front probe 162 is spaced from the left side wall by ½ λ of the operating frequency $F_f$ as shown. It will be noted that the probes each have a bent portion used for capacitive coupling with the ceiling 160 of the enclosure 166 as shown in FIG. 13. The front probe 162 is bent forward for coupling with the more forward portion of the enclosure while the back probe 164 is bent rearward for coupling with the more rearward portion of the enclosure 166 to obtain more spatial diversity and obtain better coverage by the EM field in the drawer. Other arrangements may be possible to achieve a robust field and further spatial diversity and coverage within the enclosure.

Figure 16:
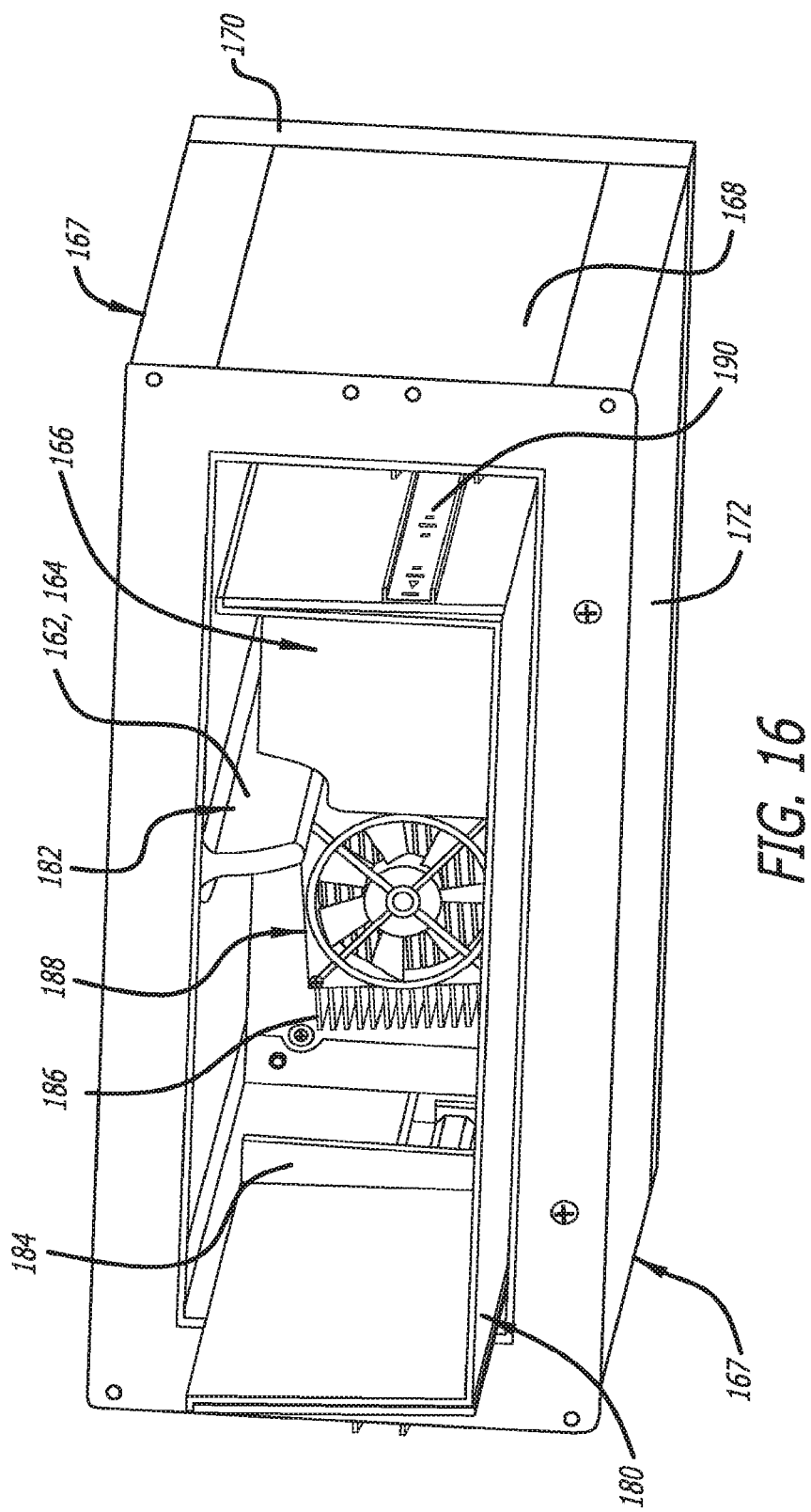
FIG. 16 is a frontal perspective view of the view of FIG. 14 with a cutaway plastic drawer in place in the metallic enclosure and further showing the dual ceiling mount probe antennae protected by an electromagnetically inert protective cover, and further showing cooling system components mounted at the back of the cabinet near the drawer's back, the drawing also showing a partial view of a drawer slide mechanism for ease in sliding the drawer between open and closed positions in the cabinet, the drawer front and rear panels having been cutaway in this view.

FIG. 16 is a frontal upward-looking perspective view of the frame 167 forming a Faraday cage 166 showing a portion of a drawer 180 that has been slidably mounted within the frame 167. The front metallic panel of the drawer has been removed so that its sliding operation can be more clearly seen. It will also be noted that the dual ceiling mount probe antennae 162 and 164 have been covered and protected by an electromagnetically inert protective cover 182. The drawer is formed of a non-metallic material, such as a plastic or other electromagnetic inert material having a low RF constant. The back 184 of the drawer has also been cut away so that a cooling system 189 comprising coils 186 and a fan 188 located in the back of the frame 167 can be seen. In this case, the drawer 180 is slidably mounted to the Faraday cage frame with metallic sliding hardware 190. The sliding hardware of the drawer is so near the side of the frame 167 of the enclosure 166 and may be in electrical contact with the metallic slide hardware of the side walls 168 of the enclosure that these metallic rails will have only a small effect on the EM field established within the enclosure.

Figure 17:
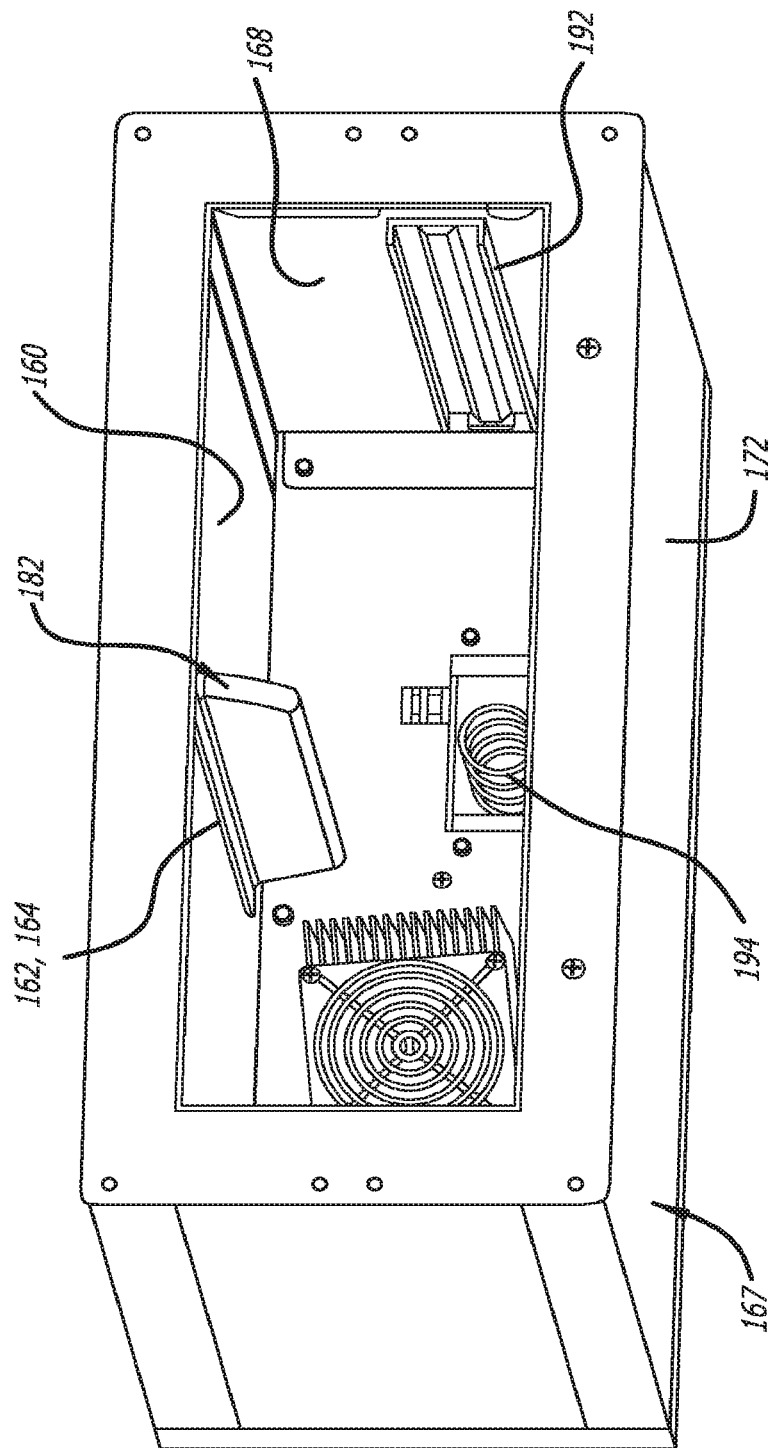
FIG. 17 is a frontal perspective view at the opposite angle from that of FIG. 16 with the plastic drawer completely removed showing the dual ceiling mount probe antennae protected by the EM inert protective cover mounted to the metallic enclosure, and further showing the cooling system components of FIG. 16 mounted at the back of the cabinet as a spring loading feature to automatically push the drawer to the open position when the drawer's latch is released, the figure also showing a mounting rail for receiving the slide of the drawer.

FIG. 17 is an upward looking, frontal perspective view at the opposite angle from that of FIG. 16; however, the drawer has been removed. The frame 167 in this embodiment includes a mounting rail 192 for receiving the slide of the drawer 180. In this embodiment, the mounting rail is formed of a metallic material; however, it is firmly attached to a side 168 of the Faraday cage and thus is in electrical continuity with the cage. The figure also shows a spring mechanism 194 used to assist in sliding the drawer outward so that access to the articles stored in the drawer may be gained. The spring is configured to automatically push the drawer outward when the drawer's latch is released.

Figure 18:
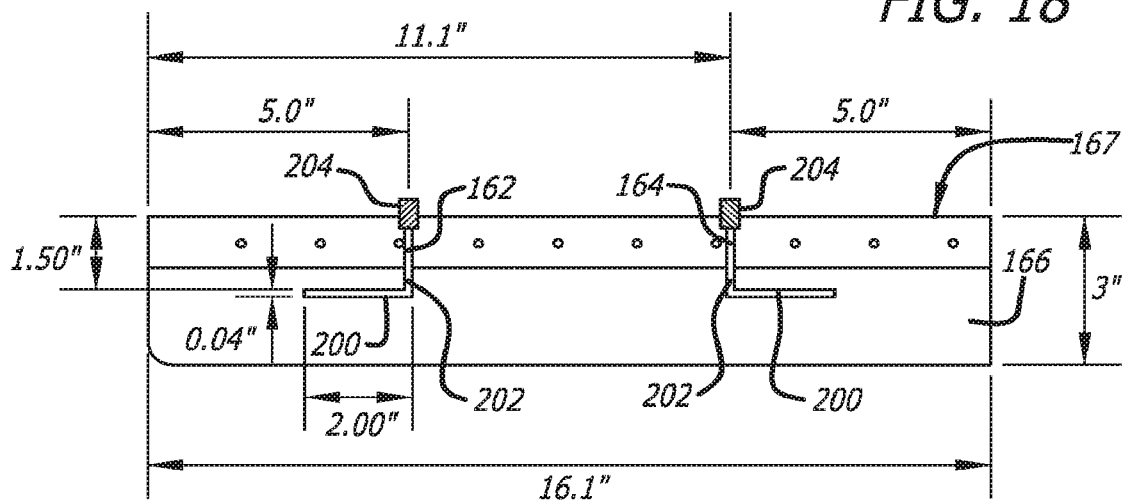
FIG. 18 is a schematic view with measurements in inches of the placement of two $TE_{01}$ mode probes in the top surface of the enclosure shown in FIGS. 13-15.

FIG. 18 is a schematic view showing measurements of the placement of two $TE_{01}$ mode capacitive coupling probes 162 and 164 in the ceiling 160 of the frame 167 shown in FIGS. 13-15. In this embodiment, the frequency of operation with the RFID tags is 915 MHz, which therefore has a wavelength of 0.32764 meters or 1.07494 feet. One-half wavelength is therefore 0.16382 meters or 6.4495 inches. The length of the capacitive coupling bent portion 200 of each of the probes is 5.08 cm or 2.00 in. The length of the axial extension 202 of the probes into the enclosure is 3.81 cm or 1.50 in., as measured from the insulator 204 into the enclosure 166. The probe configuration and placement in the embodiment was based on an operation frequency of 915 MHz. In one embodiment, the enclosure 166 had a depth of 16.1 inches (40.89 cm), a width of 19.2 inches (48.77 cm) and a height of 3 inches (7.62 cm). It was found that the optimum probe placements for this size and shape (rectangular) enclosure and for the 915 MHz operating frequency were: the front probe was spaced from the front wall by 5.0 inches (12.7 cm) and the rear probe was spaced from the back wall by 5.0 inches (12.7 cm). As discuss above, the probes in this embodiment would only be activated sequentially.

Figure 19:
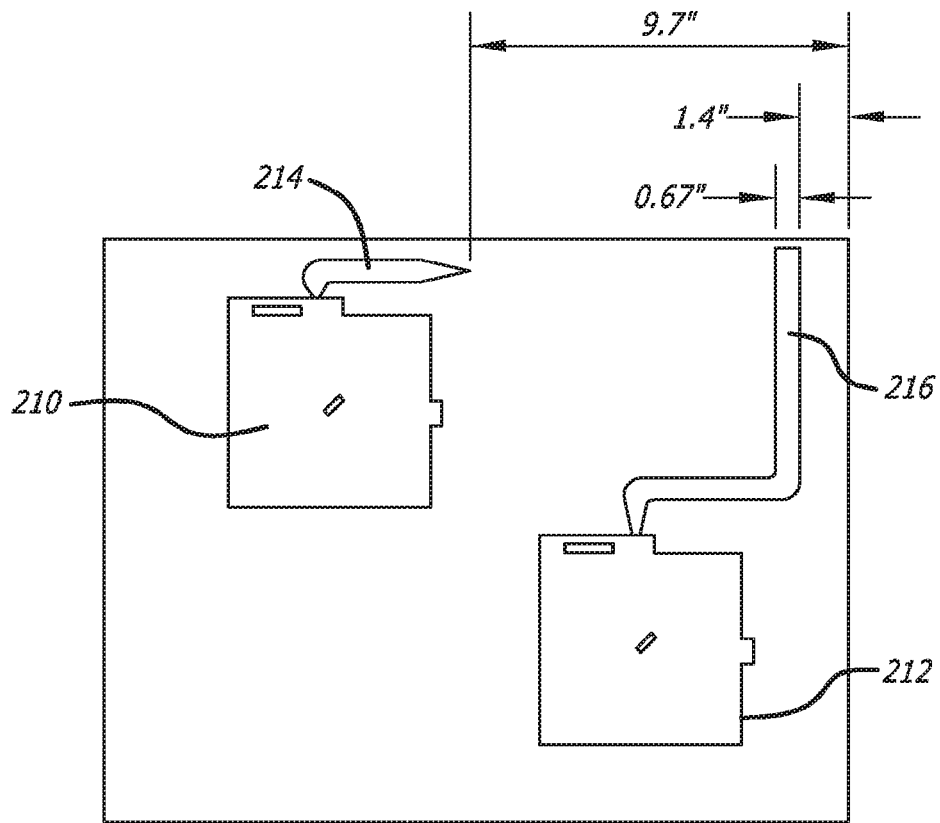
FIG. 19 is a schematic view of the size and placement within the drawer of FIG. 16 of two microstrip or "patch" antennae and their microstrip conductors disposed between respective antennae and the back of the drawer at which they will be connected to SMA connectors in one embodiment, for interconnection with other components.

FIG. 19 is a schematic view of the size and placement within the enclosure 166 of FIG. 16 of two microstrip or "patch" antennae 210 and 212 and their microstrip conductors 214 and 216 disposed between the respective antennae and the back of the enclosure at which they will be connected to SMA connectors (not shown) in one embodiment. Feed lines 58 (FIG. 3) may be connected to those SMA connectors and routed to the computer 44 for use in communicating the RFID signals for further processing. The measurements of the spacing of some of the microstrip components are provided in inches. The spacing of 9.7 in. is equivalent to 24.64 cm. The width of the microstrip line of 0.67 in. is equivalent to 17.0 mm. The spacing of 1.4 in. is equivalent to 3.56 cm. Other configurations and types of receiving antennae may be used, as well as different numbers of such antennae. In the present embodiment, the receiving antennae are mounted on insulation at the bottom inside surface of the metallic enclosure frame 167 so that the receiving patch antennae are not in contact with the metal surfaces of the Faraday cage.

Figure 20:
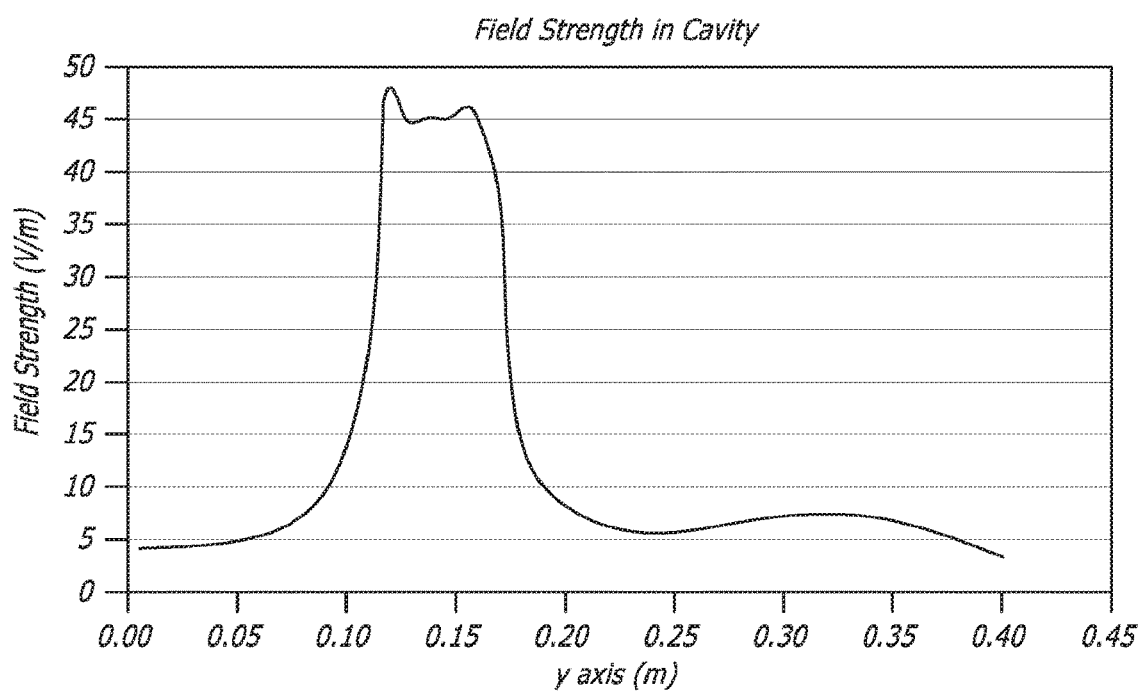
FIG. 20 is diagram of field strength in an embodiment of an enclosure with a probe placed in the enclosure at a position in accordance with the diagram of FIG. 19.
Figure 21:
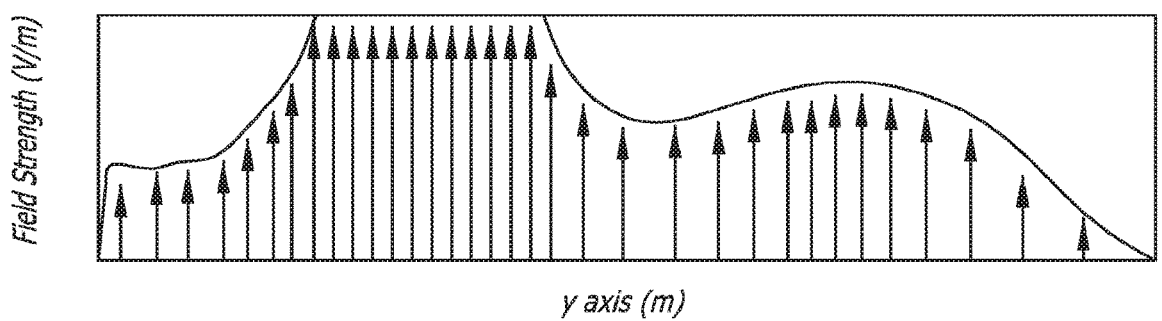
FIG. 21 is a lower scale drawing of the field intensity diagram of FIG. 20 showing a clearer view of the field intensity nearer the front and back walls of the enclosure.

Referring now to FIG. 20, the field intensity or field strength in the enclosure discussed above is shown with the ordinate axis shown in volts/meter and the abscissa axis shown in meters. It will be seen from the diagram that the maximum field intensity occurs at about 5.0 inches (0.127 m) which results from the probe positioned at 5.0 inches (12.7 cm) from the front wall and at a 915 MHz operating frequency. Referring now to FIG. 21, the scale has been reduced although the large rise in field intensity can be seen at 5.0 inches. It can also be more clearly seen that the field intensity falls off at the right wall but remains strong very close to the left wall. Therefore, in an embodiment, a second probe was used that was placed 5.0 inches (12.7 cm) from the right wall thereby resulting in a mirror image field intensity to that shown in FIG. 21. The two probes 162 and 164 are activated sequentially and are not both activated simultaneously. It will be noted that better EM field coverage of the enclosure 166 is obtained with the two probes and that RFID tags on articles positioned close to the front wall 161 will be activated by the front probe 162 and that RFID tags on articles positioned close to the rear wall 170 will be activated by the rear probe 164 (see FIG. 13).

Although not intending to be bound by theory, in deriving the probe location for TE modes in a square or rectangular non-resonant cavity, the following equation can be useful:

$$N = 2 \times \frac{L_2 - L_1}{\lambda_g}$$

where:
N=positive non-zero integer, for example 1, 2, 3, etc.
$L_1$=distance between probe and back wall
$L_2$=distance between probe and front wall
$\lambda_g$=wavelength in the cavity
$L_1$ cannot be zero for TE modes, which implies that the probe for TE mode excitation cannot be at the front or back wall. For TM modes, the equation is the same, but N can equal zero as well as other positive integers. The probe position cannot be $\lambda_g/2$ from the front or back wall. An $L_1$ and an $L_2$ are chosen such that N can be a positive integer that satisfies the equation. For example, for the enclosure 166 discussed above:
$L_1$=4.785 inches
$L_2$=11.225 inches
$\lambda_g$=12.83 inches
Therefore, $$N = 2 \times \frac{11.215 - 4.785}{12.83} = 1.0$$

The actual enclosure had the probe located at a slightly different location (5.0 inches) than that indicated by the equation (4.785 inches) which was possibly due to the insertion of a plastic drawer in the cavity, which introduces a change in the phase from the reflected signals. The equation above is set up such that the reflected phase from both front and back walls is equal, i.e., they are "in phase" at the probe location.

The wavelength in the enclosure, $\lambda_g$, can be calculated using waveguide equations. Equations for a rectangular cavity are shown below. The cutoff frequency is required for this calculation. The equations will change for a cylindrical cavity or for other shapes.

The cutoff frequency is at the point where g vanishes. Therefore, the cutoff frequency in Hertz is:

$$(f_c)_{mn} = \frac{1}{2\pi\sqrt{\mu\varepsilon}}\sqrt{\left(\frac{m\pi}{a}\right)^2 + \left(\frac{n\pi}{b}\right)^2} \text{ (Hz)}$$

The cutoff wavelength in meters is:

$$(\lambda_c)_{mn} = \frac{2}{\sqrt{\left(\frac{m}{a}\right)^2 + \left(\frac{n}{b}\right)^2}} \text{ (m)}$$

where:
=inside width
b=inside height
m=number of ½-wavelength variations of fields in the "a" direction
n=number of ½-wavelength variations of fields in the "b" direction
ε=permittivity
μ=permeability The mode with the lowest cutoff frequency is called the dominant mode. Since $TE_{10}$ mode is the minimum possible mode that gives nonzero field expressions for rectangular waveguides, it is the dominant mode of a rectangular waveguide with a>b and so the dominant frequency is:

$$(f_c)_{10} = \frac{1}{2a\sqrt{\mu\varepsilon}} (Hz)$$

The wave impedance is defined as the ratio of the transverse electric and magnetic fields. Therefore, impedance is:

$$Z_{TE} = \frac{E_x}{H_y} = \frac{jw\mu}{\gamma} = \frac{jw\mu}{j\beta} \Rightarrow Z_{TE} = \frac{k\eta}{\beta}$$

The guide wavelength is defined as the distance between two equal phase planes along the waveguide and it is equal to:

$$\lambda_g = \frac{2\pi}{\beta} > \frac{2\pi}{k} = \lambda$$

where $k_c = \sqrt{\left(\frac{m\pi}{a}\right)^2 + \left(\frac{n\pi}{b}\right)^2}$ ; and $$\beta = \sqrt{k^2 - k_c^2}$$

Figure 22A:
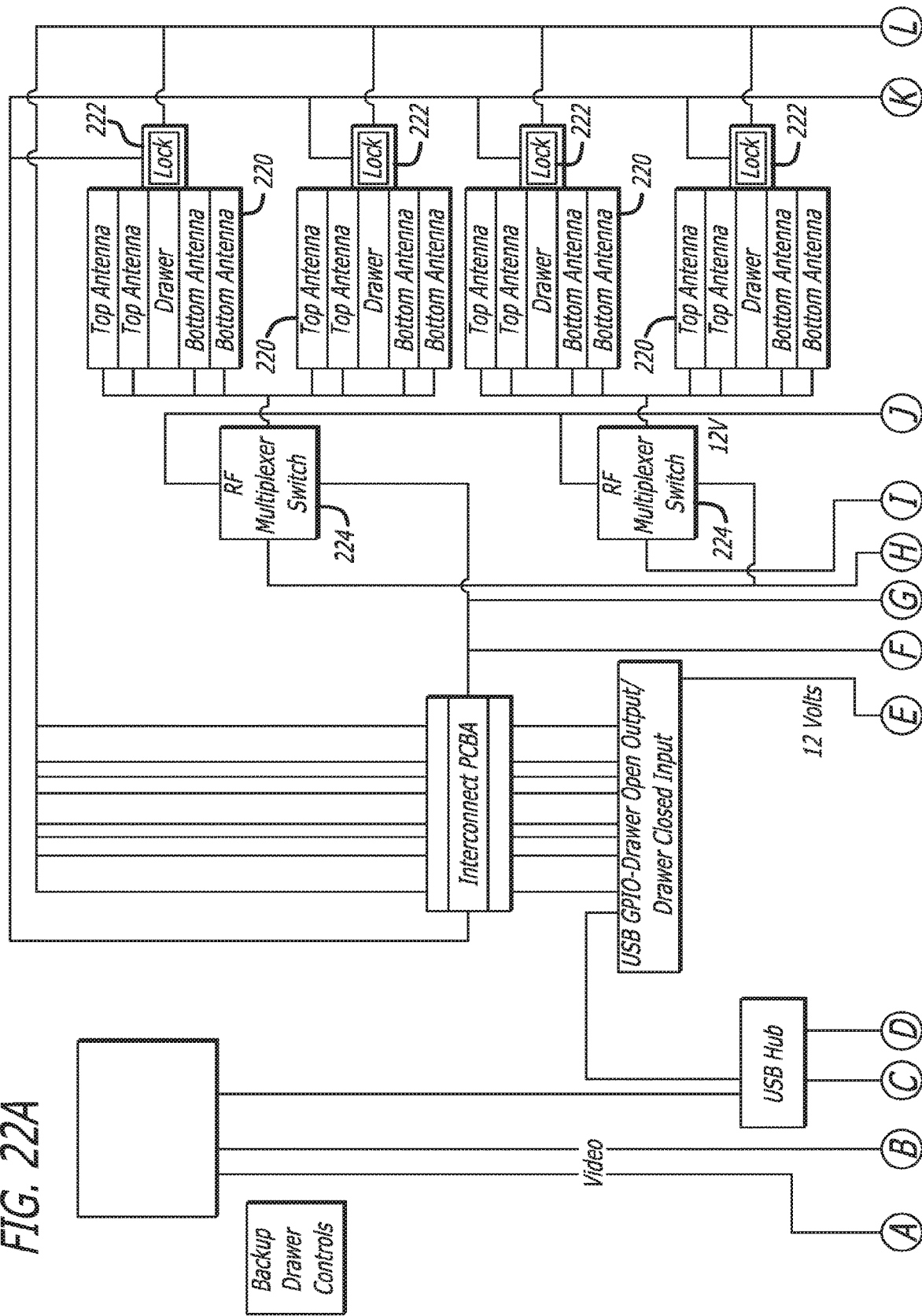
FIGS. 22A and 22B together present a block electrical and signal diagram for a multiple-drawer medical cabinet, such as that shown in FIG. 2, showing the individual multiplexer switches, the single RFID scanner, and power control.
Figure 22B:
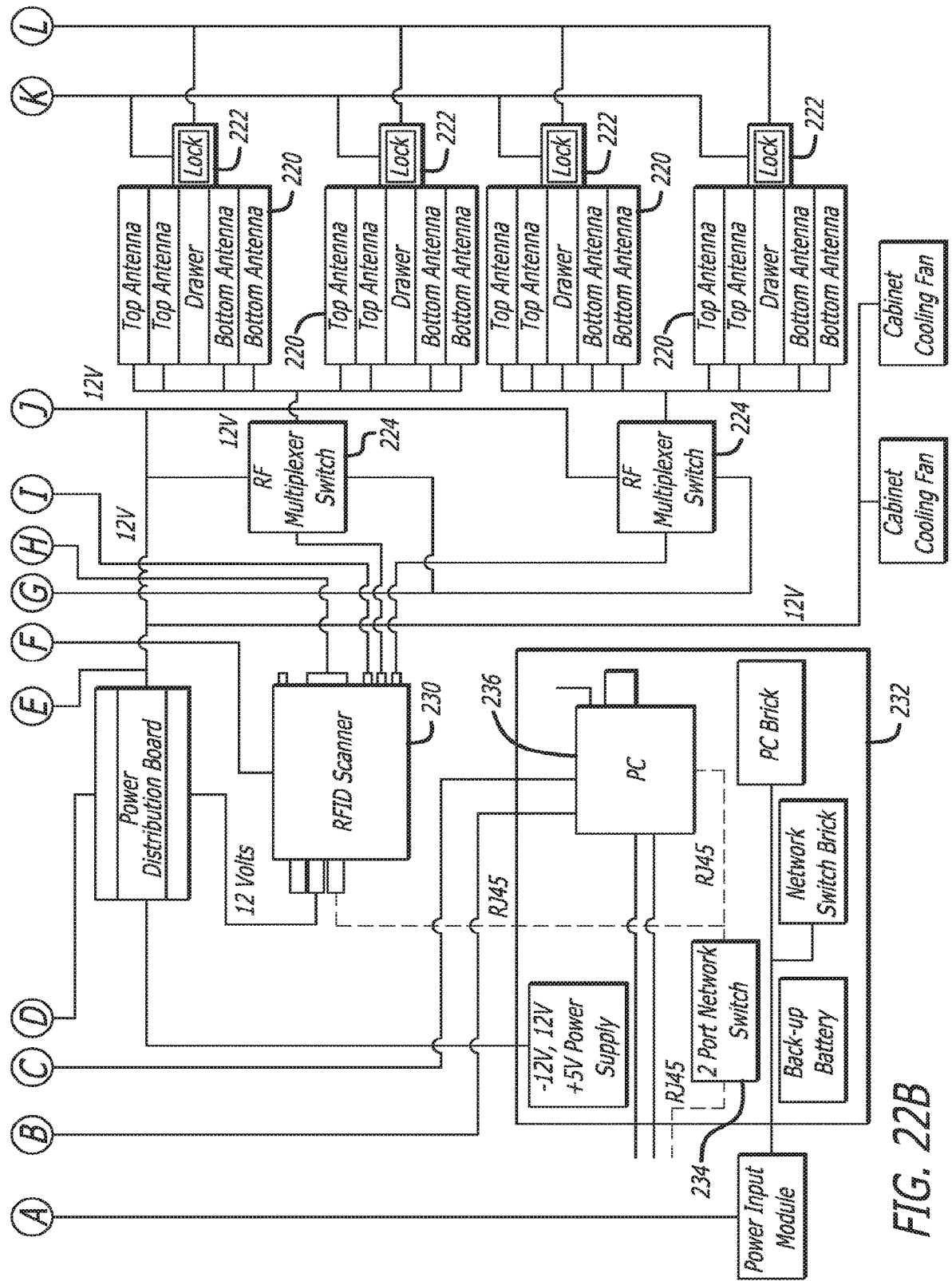
Figure 24:
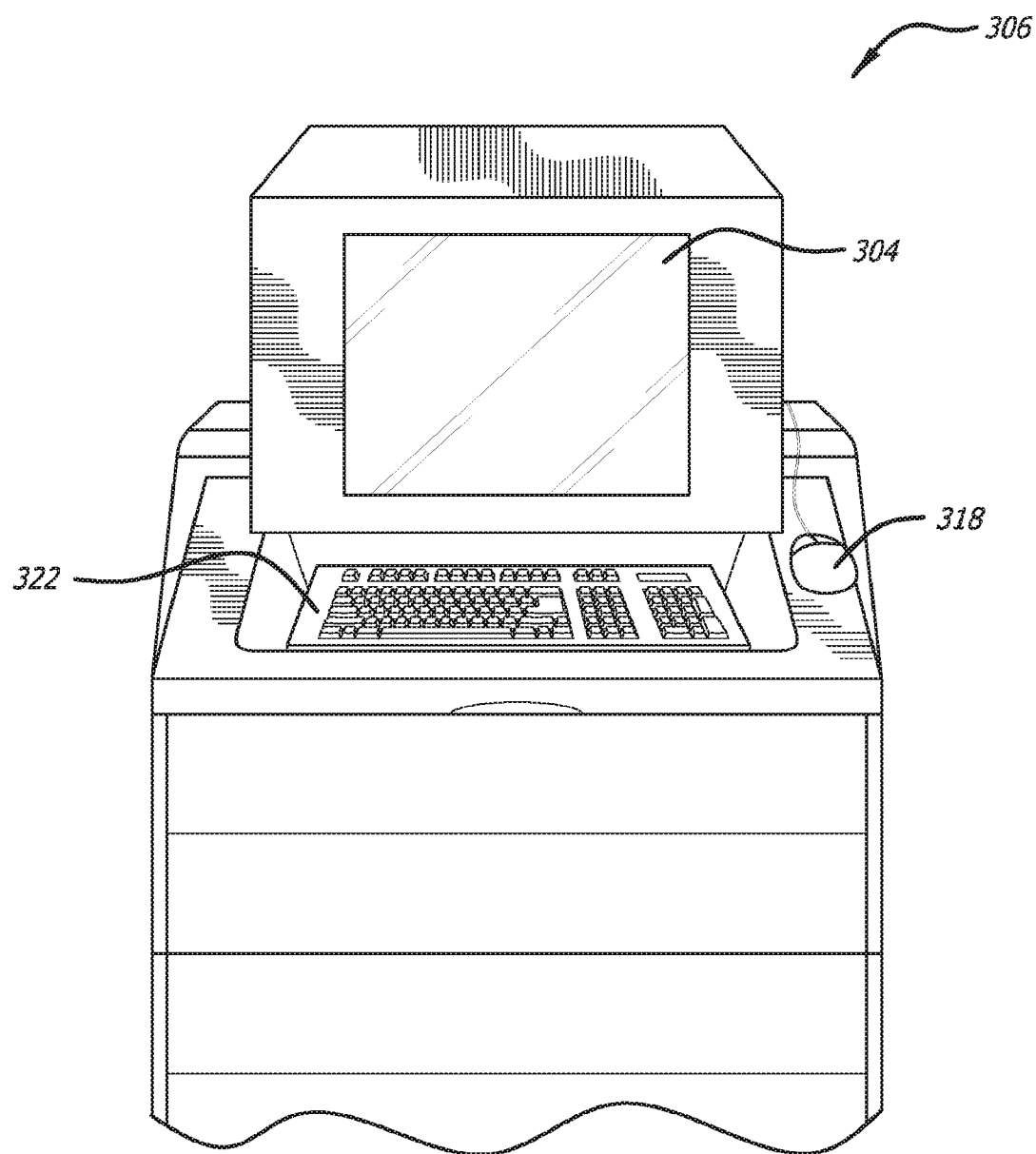
FIG. 24 shows the medication administration cabinet of FIG. 23 with a view of two input devices, one of which is a full size keyboard and the other of which is a pointing device in the form of a mouse.

FIGS. 22A and 22B together provide a block electrical and signal diagram for a multiple-drawer medical cabinet, such as that shown in FIG. 2. In this case, the cabinet has eight drawers 220, shown in both FIGS. 22A and 22B. Each drawer includes two top antennae, two bottom antennae and a lock with a lock sensor 222 for securing the drawer. Signals to and from the antennae of each drawer are fed through an RF multiplexer switch 224. Each RF multiplexer switch 224 in this embodiment handles the routing of RF signals for two drawers. RFID activation field and RFID received signals are fed through the respective RF multiplexer switch 224 to a main RFID scanner 230 (see FIG. 22B). The scanner 230 output is directed to a microprocessor 232 (see FIG. 22B) for use in communicating relevant information to remote locations, in this case by wired connection 234 and wireless connection 236 (see FIG. 22B). Various support systems are also shown in FIGS. 22A and 22B, such as power connections, power distribution, back up battery (see FIG. 22B), interconnection PCBA, USB support (see FIG. 22A), cooling (see FIG. 22B), and others.

In accordance with one embodiment, drawers are sequentially monitored. Within each drawer, the antennae are sequentially activated by the associated multiplexer 224. Other embodiments for the signal and electrical control systems are possible.

Although RFID tags are used herein as an embodiment, other data carriers that communicate through electromagnetic energy may also be usable. RF energy is also discussed at length but EM energy of other forms may also be usable.

Self-Contained Drawer Module

In accordance with aspects of the invention, a medication cabinet that does not include a built-in RFID detection system can be RFID enabled, or transformed, or retro-fitted, to become one that allows for the automatic identification and tracking of inventory. Similarly, a cabinet that is being built may be fitted during the time of building with the RFID-enabling system disclosed here to make that cabinet, drawer, or drawers an automatic system with which automatic inventorying for identification and tracking may be performed. The system herein is applicable not only to medication cabinets, but may also be employed in other types of containers of items. Cabinets are used herein only as an example and the invention is not limited to use with only them.

In accordance with the RFID-enabling system disclosed here, a self-inventory can be conducted on any basis. Items within the container that is RFID-enabled according to the disclosure herein can be identified and tracked at any time. For example, such self-inventorying can automatically occur in the middle of the night, or once each hour, every time a drawer or container is opened, or more often, or less often. Complete flexibility and versatility are provided with reduced labor requirements. As is discussed below, many advantages flow from this design.

Figure 25:
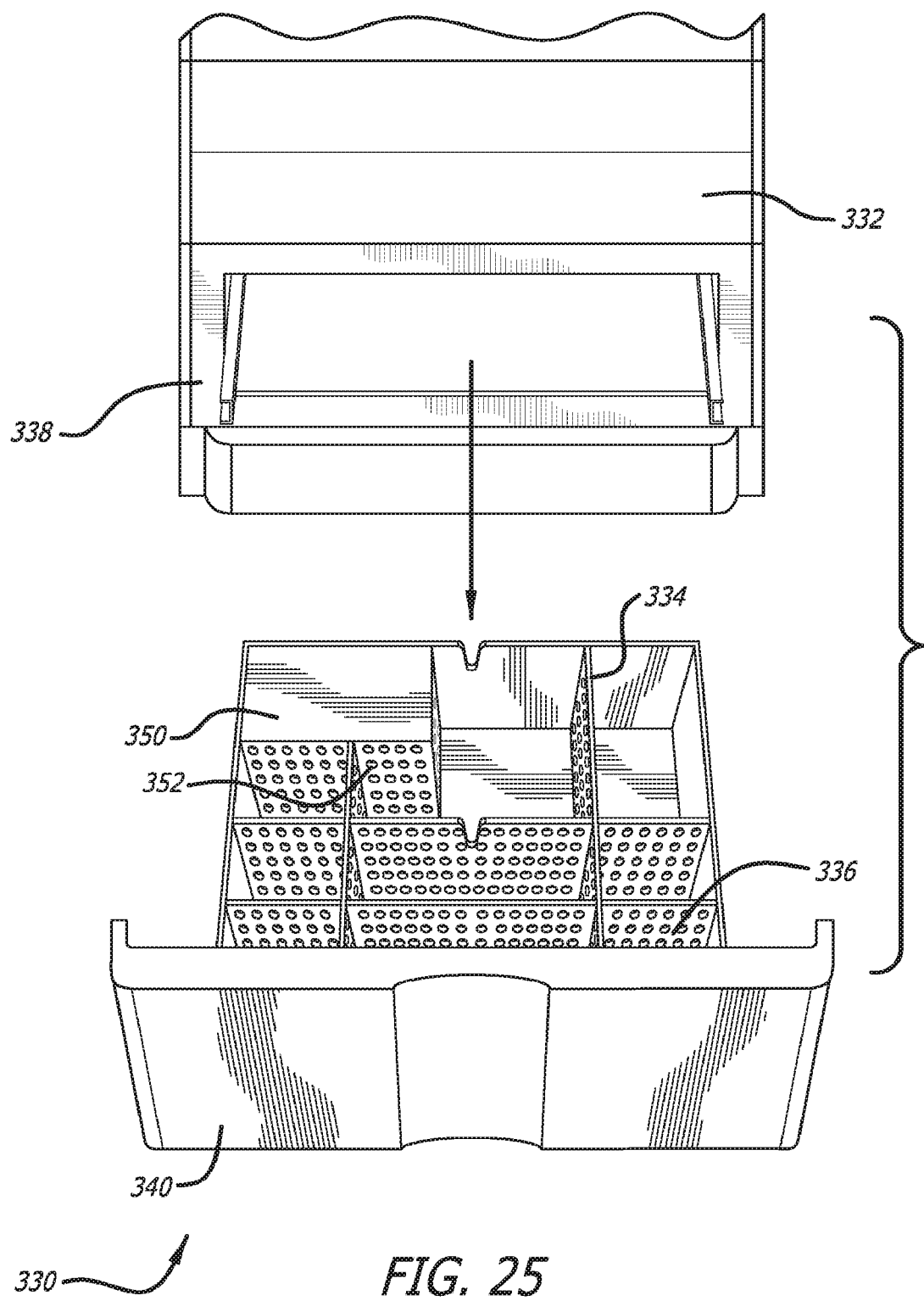
FIG. 25 is an exploded view of a drawer removed from the opening and Faraday cage of the medication cabinet, showing details of the drawer design including partitions for creating pockets to store medical items, and part of the Faraday cage created in the cabinet.
Figure 26:
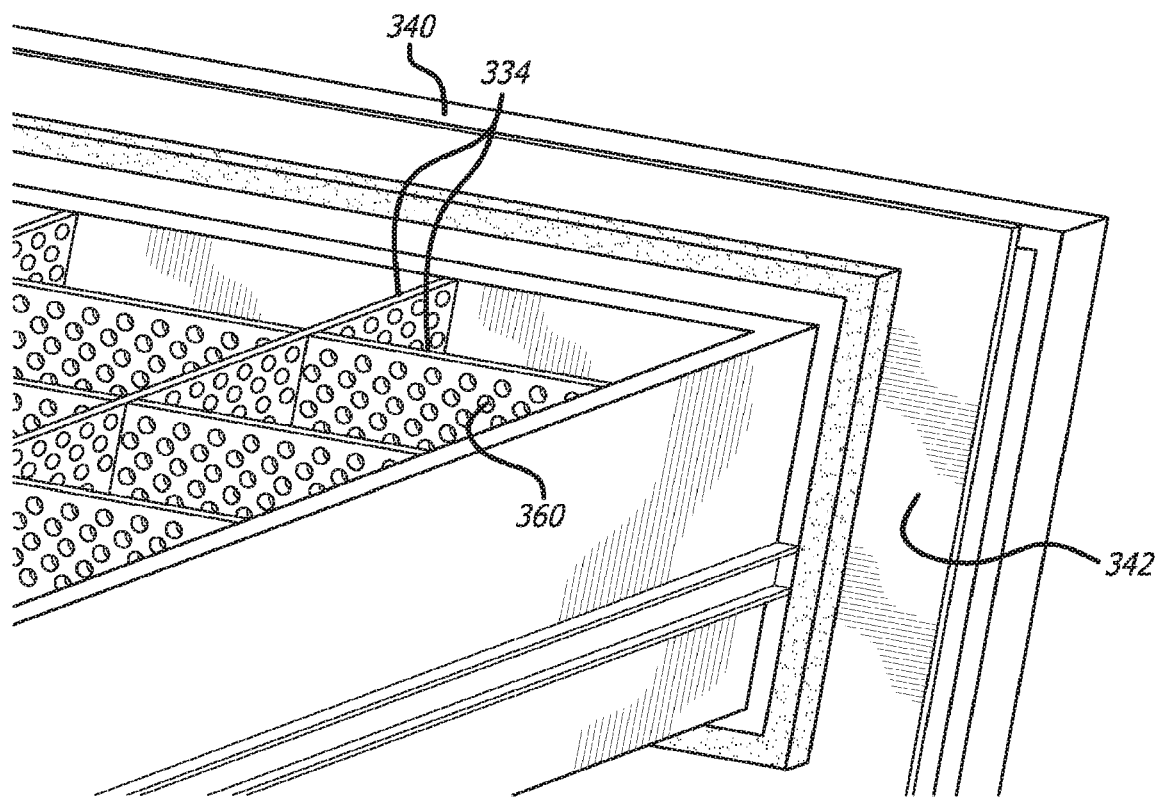
FIG. 26, is an enlarged view of the drawer of FIG. 25 looking from behind the drawer so that a metallic front of the drawer can be seen to form a part of a Faraday cage, which, when the drawer is in the closed position, completes the Faraday cage about the drawer so that the RFID system will operate effectively.

Referring now to FIG. 25, a non-metallic slidable drawer 330 is configured to be mounted within a medication cabinet 332. It includes various dividers or partitions 334 in the drawer that form "pockets" 336 within which are placed medical articles such as medications for storage and administration. In this embodiment, the cabinet within which the drawer is slidably mounted includes a metallic frame 338 surrounding the drawer to operate as a Faraday cage. Also now referring to FIG. 26, the front portion 340 of the drawer 330 may be formed of metal 342, or where the drawer is non-metallic, include a metallic portion sized and placed to contact the remainder of the metallic frame 338 of the cabinet 332 when the drawer is in the closed configuration to complete the Faraday cage around the drawer. By installing the self-contained RF drawer module described herein within the Faraday cage of the drawer, that frame will have within it an RF system for detecting the existence of RFID tagged articles placed in the drawer.

In an embodiment shown in FIG. 23, a data base 320 is used so that a healthcare institution can maintain a list of medications and other medical supplies prescribed for patients or for stocking in the medication cabinet for general use.

Figure 27:
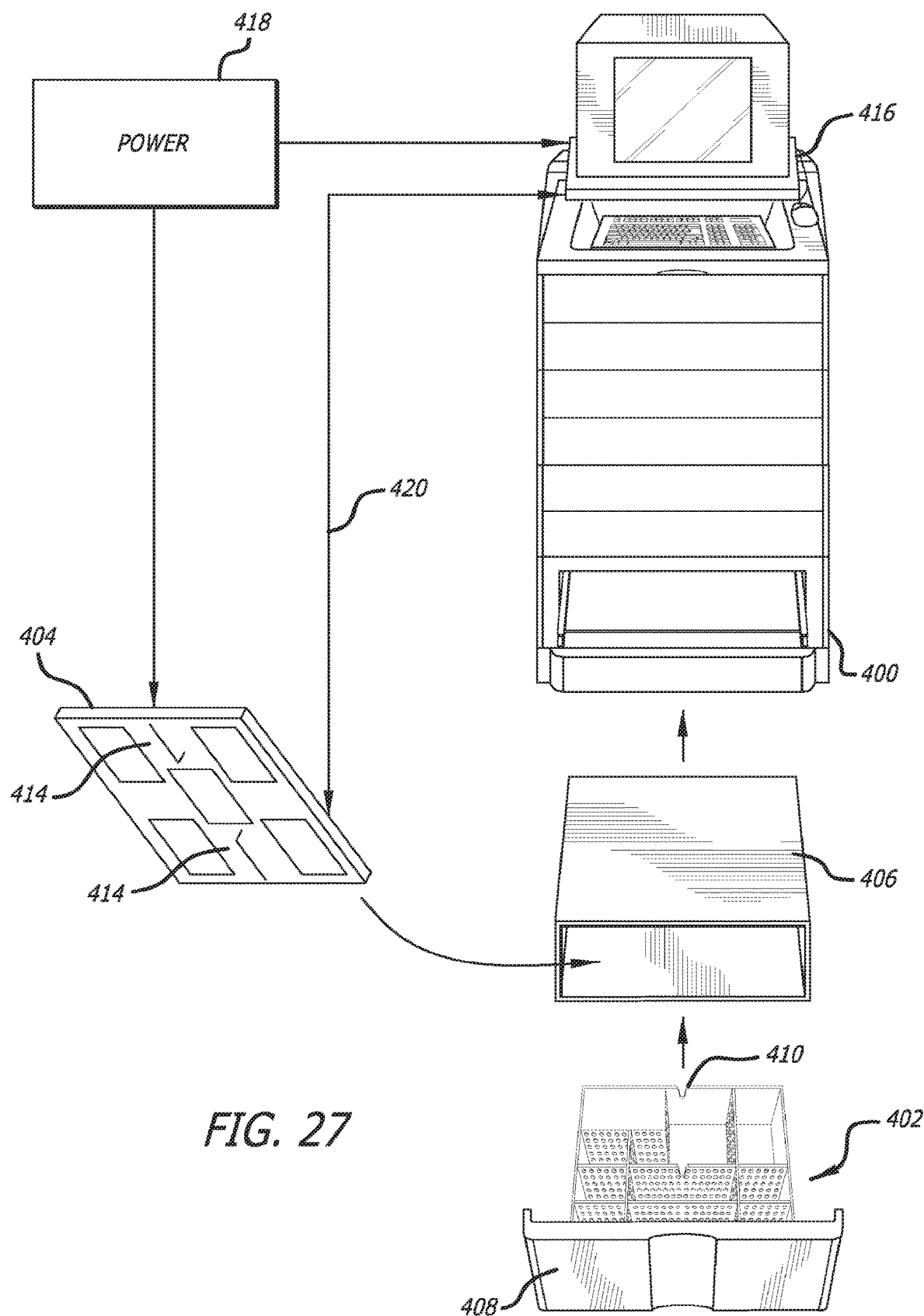
FIG. 27 is an exploded view of a medication cabinet with the lower drawer removed, showing a representation of a Faraday cage to be formed within the frame for the removed drawer, an RFID-enabling module, to be mounted with the Faraday cage so that at least the antennae of which are within the Faraday cage, and the drawer to be slidably mounted within the representation of the Faraday cage, and also showing power and data connections for the module.

In FIG. 27 there is shown a medication cabinet 400 having its bottom drawer 402 removed. In this case, the bottom drawer is formed of plastic and does not provide a Faraday cage for use in RFID enabling the drawer. Also shown is an RFID-enabling drawer module 404 designed to provide an environment in the removed drawer 402 in which items having RFID tags placed in the drawer can be detected, identified, and tracked. As will be described in some detail below, the module in this embodiment includes probe antennae and receiving antennae that must be mounted within a Faraday cage formed by or formed around the drawer 402. Because the RFID-enabling module disclosed herein can generate a robust EM field in a container regardless of the resonant frequency of that container, retrofitting a drawer such as shown in FIG. 27 becomes possible. The robust EM field created by the RFID-enabling module system is able to activate all RFID tags within the drawer so that they may be read and the item to which they are attached can be identified and tracked.

Because the present drawer 402 is formed of plastic, a Faraday cage must be formed around it. Accordingly, a Faraday cage, represented schematically in FIG. 27 as a box 406, is formed around the drawer. In the embodiment shown, it may comprise metallic walls that are mounted within the frame of the cabinet 400 to completely enclose the drawer once is it reinserted into the cabinet and closed. The metallic walls may be formed by various ways, one of which is to install metallic foil about the drawer in the frame. The foil should be large enough to engage the front 408 of the drawer to complete the cage. The drawer front may be painted with metallic paint on the outside, sides, and inside the front panel to make contact with the foil and provide a cage completely across the front of the drawer. As another embodiment, metallic paint may be used within the frame of the cabinet to create the Faraday cage. Other means may also be used to construct or complete the Faraday cage to surround the container in which items are being identified and tracked.

In an embodiment where the drawer is metallic and itself forms a Faraday cage, the antennae of the module 404 must be mounted to be within the cage to communicate with the field and RFID transmissions within the cage. In some cases, the module is placed above the drawer and in other cases, it may be placed below the drawer, depending on the configuration of the cabinet and the drawer. Additionally more than one drawer in a cabinet can be RFID enabled, according to aspects of the invention.

As mentioned, the module 404 can be mounted above the drawer to RFID-enable the drawer. In the embodiment shown in FIG. 27, the module has two probe antennae 414 that protrude above its surface by a certain distance. In this case, they are centered on the module. To accommodate those antennae, a notch 410 has been formed in the back of the drawer so that the drawer back will not damage the probe antennae when the drawer is pulled to the open position and pushed to the closed position. If there are partitions within the drawer, as shown in FIG. 25, notches 412 may also be formed in those. As shown in FIG. 17, these probe antennae may be covered by a protective cover 182. The module 404 may be mounted within the Faraday cage by standoffs and screws into the ceiling of the frame around the drawer. Other mounting techniques are possible.

FIG. 27 also shows connection of the module to a power source 418 and to data communications 420 with a local computer 416. In the embodiment where the module 404 is connected to an Ethernet (not shown), the power may be provided entirely by the Ethernet connection (Power over Ethernet or "PoE"). Additionally, the local computer 416 may be programmed to process RFID data of identified and tracked items by the module 404 in the RFID-enabled drawers 402 of the cabinet 400, and may also be programmed to create a data base of those items and the RFID data associated with them. The processed RFID data and the data base may be communicated to a central server 310 and its data base 320 as shown in FIG. 23, or may be communicated elsewhere or to additional locations. It also may be communicated to a cart 316, also shown in FIG. 23. At the central server, a program may configure the server to process the received RFID and item data further, as necessary. The local computer 416 would also contain a data base of the installed hardware, the hardware address correlated to which drawer, and other various data base items. Since construction of such a program and data base are well within the skill of those in the art, no further detail is provided here.

Figure 28:
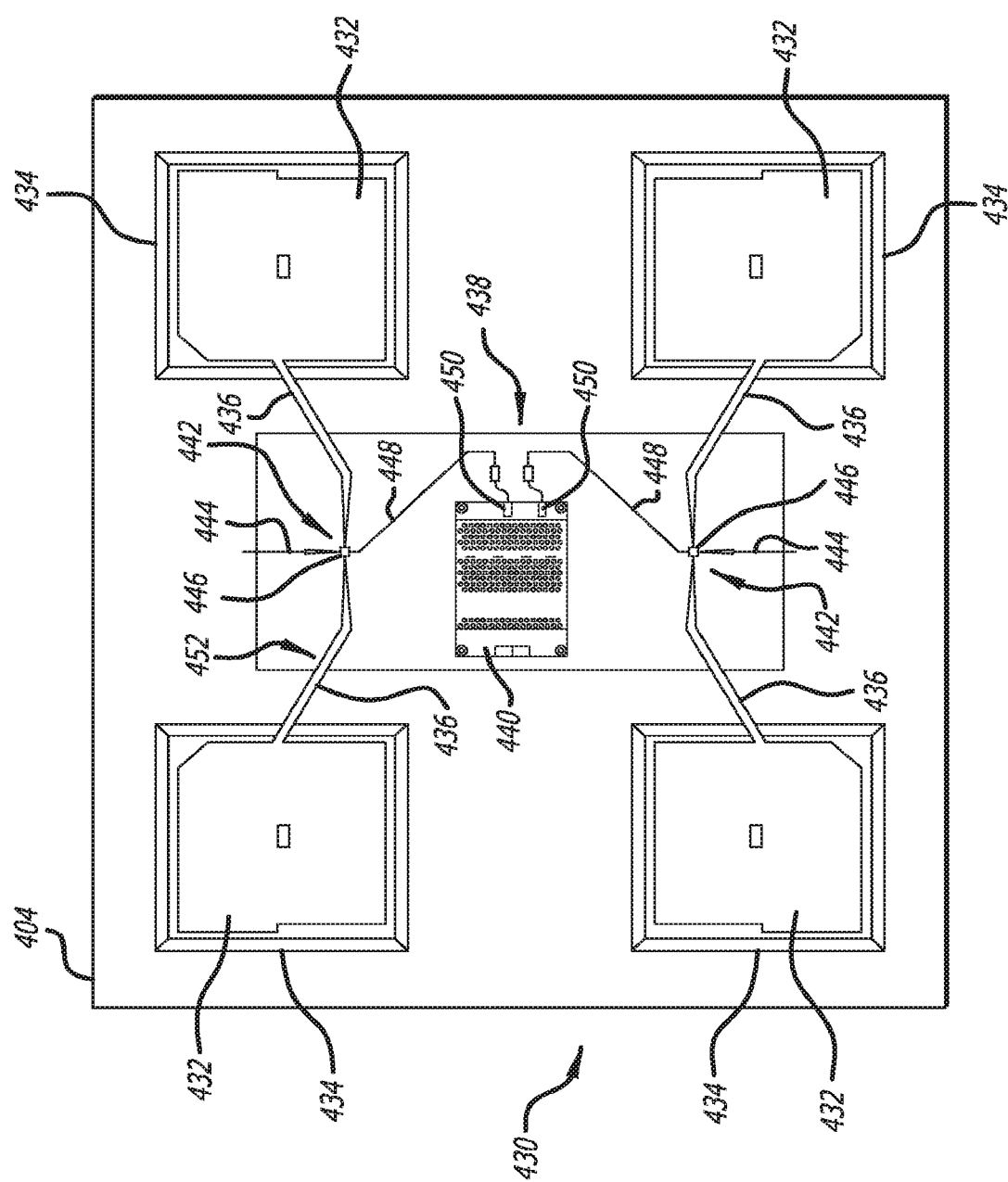
FIG. 28 is a top view of an RFID-enabling drawer module in accordance with aspects of the invention showing four receiving antenna elements, two probe antennas, an RFID reader printed circuit board, an RFID reader mounted to the RFID reader printed circuit board, and two switches, each of which interconnects two antenna elements and interconnects the probe antennas with the RFID reader.

Now turning to FIG. 28, the RF drawer module 404 is composed of two main systems, a plastic base and a RFID reader/antenna printed circuit board. The plastic base 430 is approximately nineteen inches (48 cm) by sixteen inches (41 cm), or generally the size of the RF enabled drawer 402. The plastic base includes four areas where patterned conductive material, in the shape of an antenna radiating element 432, has been thermoformed into a mesa structure 434. The antenna radiating element has been optimized for the height of the mesa and the dielectric of air. The plastic base rests on a metal surface, part of the shielded drawer enclosure that is the ground reference for the antenna radiating element. The conductive material is patterned on the top of the plastic base and includes conductive traces 436, on both the mesa and plastic base, for connecting the radiating element to the RFID reader printed circuit board 438.

The RFID reader/antenna printed circuit board 438 has been designed to accommodate a RFID reader module 440, two X4 RF switches 442, mounting pads 446 for two probe antennas 444, and traces 436 for connecting the switches to the patch antennas 432 on the plastic mesas 434. The printed circuit board includes mounting holes for mechanically attaching the RFID reader module to the printed circuit board. The printed circuit board includes power conditioning, USB interface, and Power over Ethernet circuitry to support the RFID reader module 440. The two RF ports 450 of the RFID reader module 440 connected to the printed circuit board via two MMCX to MMCX coax cables. The signals from these cables are each connected 448 to the input of an X4 RF switch 442. The four outputs of each of the two X4 RF switches are connected as follows: a solder position for one probe antenna; interconnect traces for two patch antenna; and one spare output with no connection.

The RFID reader printed circuit board 440 is mechanically attached to the center of the plastic base 430. The printed circuit board interconnect traces and plastic base conductive traces have been designed to coincide, resulting in a capacitive coupled connection 452 between the printed circuit board and the antenna elements on the thermoformed plastic base.

Figure 29:
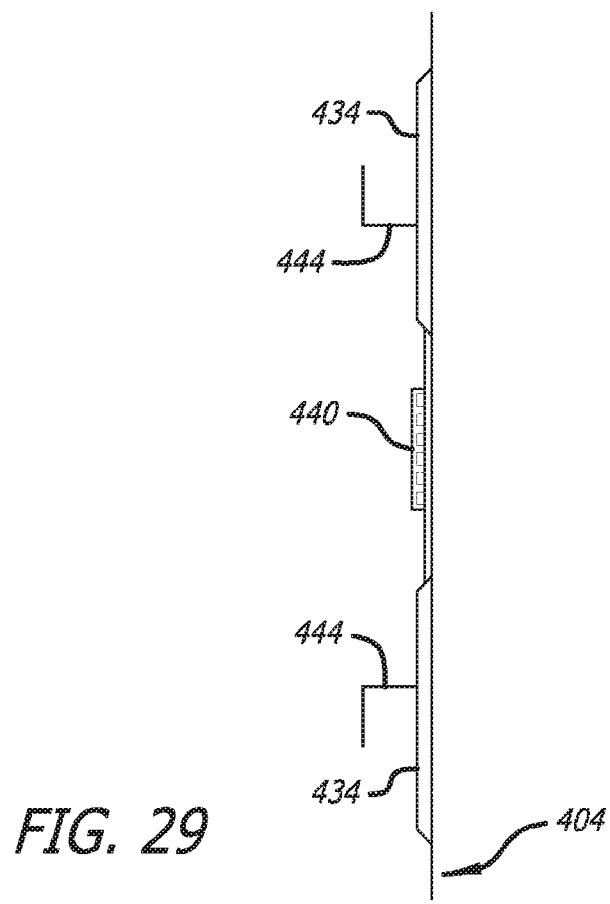
FIG. 29 is a side view of FIG. 28 that more clearly shows the side profile of the two probe antennas and mesa structures upon which the antenna elements are formed.
Figure 30:
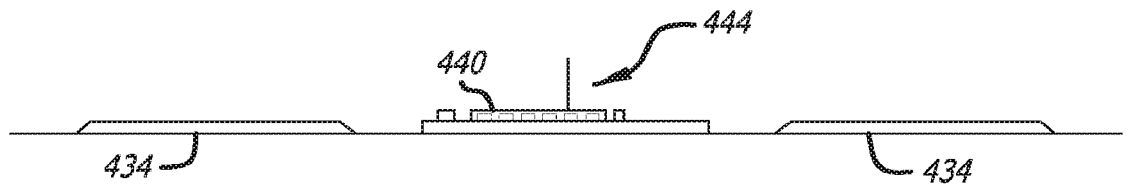
FIG. 30 is a front view of FIG. 28 that shows the end profile of a probe antenna, the RFID reader, and the mesa structures on which antenna elements are mounted.

FIG. 29 presents a side view of FIG. 28 and shows two mesa structures 434 behind which are probe antennae 444. The RFID reader module 440 can also be seen. Similarly, FIG. 30, which is an end view of FIG. 28, also shows two mesas 434, a probe antenna 444, and the RFID reader 440.

Implementation of the RF drawer module 404 results in the following:

1. Improved RF signal integrity;
2. Simplification of RF enabled drawer assembly, maintenance, and repair;
3. Improved RF drawer reliability; and
4. Modular product configuration (an RFID-enabled drawer can be sold as one unit or part of a cabinet containing several drawers).

The self-contained RFID-enabled drawer module 404 may be positioned at a location next to a medication drawer, or other type of drawer or container, to provide detection of the contents of the drawer through RFID technology, or other technology. The drawer may be slidable into and out of a medication cabinet 400, for example, and when slid into the cabinet, the module may be made operable to detect and identify the RFID-tagged articles in the drawer. The module 404 in accordance with the above description and the accompanying drawings may be used to establish a complete detection system at a drawer with only the need for connection to power and data communications lines, as needed. Depending on the size of the drawer, more or fewer antenna elements and more or fewer probe antennae may be used. Also, different locating structures may be used; for example, the mesa structures disclosed may not be used, or may take a different form. As another example, the RFID reader printed circuit board may take a different form or may be integrated with a base in another way.

The system disclosed herein results in ease of manufacturing RFID-enabled drawer systems. The RFID-enabling module becomes a drop-in component inside the Faraday cage. The design allows for retro-fitting of some of the existing drawer-based cabinet systems. Because it generates a robust EM field in a container, regardless of the resonant frequency of that container, it is useful for a large range of drawers and containers. As an example, it is useful for a "single" drawer, for "double" drawers, and others. It further allows for automatic tuning, or dynamic tuning, of antennae based upon the size and loading of the Faraday cage. For example, as more tagged items are placed within a drawer, the "loading" in the drawer changes because more items now reside within the RF field of the Faraday cage. Conversely, as items are removed, the loading of the RF field changes also. Such automatic tuning is known to those of skill in the art and further detail is not provided herein. See for example U.S. Pat. No. 7,812,774 to Friman et al. and U.S. Pat. No. 7,830,320 to Shamblin et al. Furthermore, the RFID-enabling module is a self-contained module with only power and communication ports visible, thereby eliminating the SMA connectors and RF cables. This reduces assembly and testing costs, and greatly improves the serviceability of the system.

The above benefits include at least the following:
Self-inventory capability for multiple items at one time;
Ability to verify inventory against minimum/maximum inventor levels and a means for reordering;
Medication error prevention;
Counterfeit prevention;
ePedigree/serialization capability;
Lot control;
NDC control;
Expiration control;
Data mining; and
It provides a data base system and therefore results in the ability to monitor and associate a specific RFID tag with ancillary information pertinent to the item to which it is affixed.

Configuring systems and processors to receive, transmit, and manipulate data to provide the benefits listed above in conjunction with the RFID-enabling module system disclosed herein is known to those of skill in the art, and is not described further herein. See U.S. Pat. No. 7,140,542 to Andreasson et al. and U.S. Pat. No. 7,175,081 to Andreasson et al., both of which are incorporated herein by reference and both of which are assigned to the assignee of the present invention.

Figure 31:
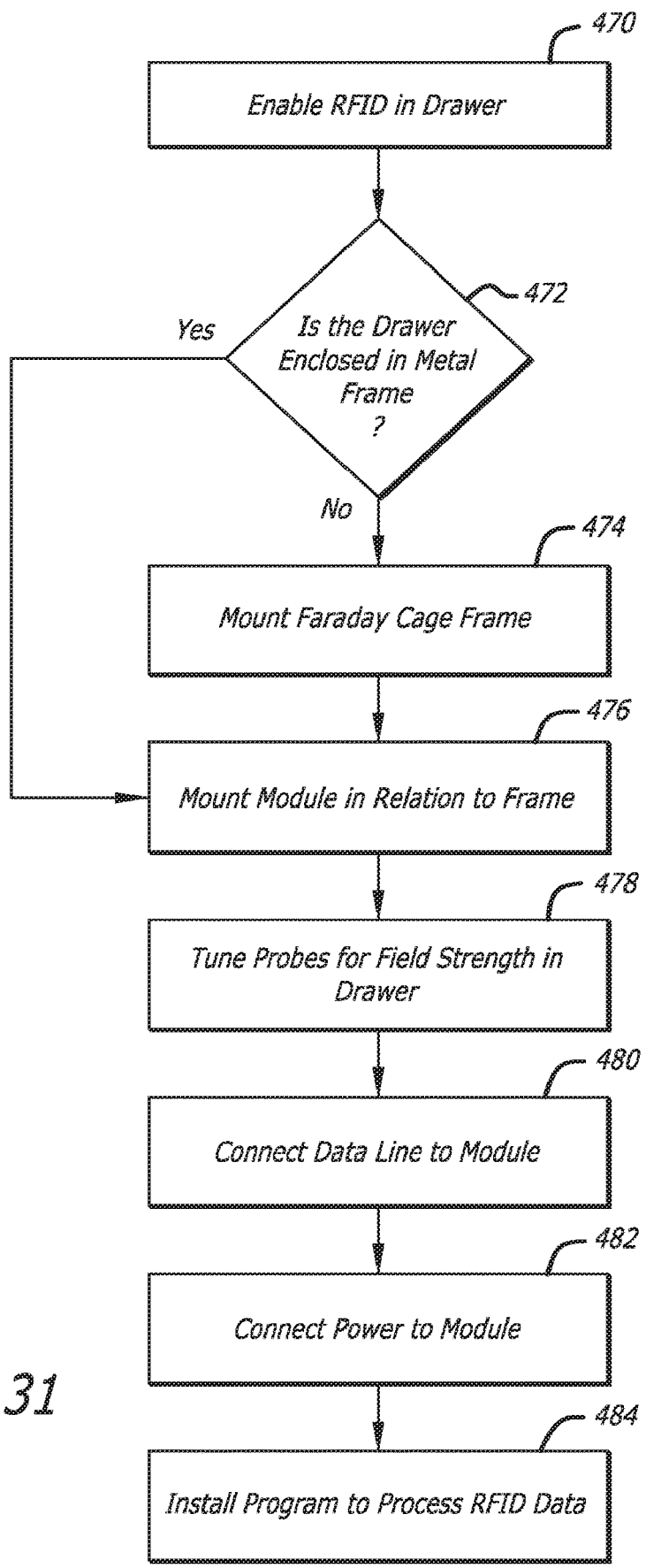
FIG. 31 is a flow chart presenting a method by which a drawer is RFID enabled in accordance with aspects of the invention.

FIG. 31 presents a method in accordance with aspects of the invention. When a drawer is to be RFID enabled 470, it is inspected to determine if it is located within a Faraday cage structure 472 when it is in the closed position. If it is not within a Faraday cage, action is taken 474 to locate one completely around the drawer so that a suitable EM field can be established with in the drawer to detect RFID tags. Once the Faraday cage has been successfully established, the RFID enabling module is mounted 476 in the cabinet in relation to the drawer so that it can detect such RFID tags in the drawer. The probe antennae are tuned to establish the highest field strength throughout the drawer 478. The data line or lines 480 and power 482 are connected to the RFID enabling module. An appropriate processor-configuring program is installed so that the RFID tag data can be processed whereby the items associate with the RFID tags can be identified and tracked.

As used herein for convenience, the well-known Faraday cage or Faraday shield or Faraday cavity is an enclosure formed by conducting material or by a mesh of such material. Such an enclosure blocks out external static electric fields.

Unless the context requires otherwise, throughout the specification and claims that follow, the word "comprise" and variations thereof, such as, "comprises" and "comprising" are to be construed in an open, inclusive sense, which is as "including, but not limited to."

While the invention has been described in connection with what is presently considered to be the most practical and preferred embodiments, it is to be understood that the invention is not to be limited to the disclosed embodiments and elements, but, to the contrary, is intended to cover various modifications, combinations of features, equivalent arrangements, and equivalent elements included within the spirit and scope of the appended claims.

We claim:

1. A retrofit RF (radio frequency) enabling module for automatically identifying and tracking an inventory of medical articles located in a container, the container having electrically-conductive walls within which the medical articles are located, each of the medical articles having an attached identification device that is activated by RF energy and which responds to activation by sending an identification signal, the retrofit RF-enabling module comprising:
a base having a size selected to be dropped into and mounted within the electrically-conductive walls of the container, the base having a data port and a power port;
a probe located on the base and configured to inject an activating RF field within the container for activating the identification devices of the medical articles located within the container;
a reader unit located on the base and having a communications unit with which it connects to the data port, the reader unit also having a control unit connected with the power port and the communications unit, the control unit configured to use power received from the power port to control the probe to inject power into the container to establish an activating RF field within the container, the control unit also configured to control the probe to stop injecting energy into the container and during the non-injection time, to receive the identification signals from the activated identification devices on the medical articles located within the electrically-conductive walls of the container, to process those signals, and to deliver data representative of the received identification signals to the data port through the communications unit.

2. The retrofit RF-enabling module of claim 1 further comprising an Ethernet port, through which power is received at the base and through which data is received by the base and exported by the base.

3. The retrofit RF-enabling module of claim 1 wherein the probe is configured to automatically retune itself to establish the activating RF field within the container to accommodate more or fewer medical articles in the container.

4. The retrofit RF-enabling module of claim 1 further comprising multiple probes located on the base apart from each other, and wherein the reader unit is centrally located on the base between the multiple probes.

5. The retrofit RF-enabling module of claim 1 comprising a switch mounted to the base and connected to the probe, the control unit being further configured to control the switch to apply energy to the probe to be injected into the container and further configured to control the switch to stop the injection of energy by the probe into the container.

6. The retrofit RF-enabling module of claim 1 wherein the reader unit is configured to automatically establish the activating RF field in the container according to a schedule.

7. The retrofit RF-enabling module of claim 1 wherein the control unit is configured to control the probe to automatically retune itself to establish the activating RF field within the container to accommodate more or fewer items in the container.

8. The retrofit RF-enabling module of claim 1 further comprising a matching circuit connected with the probe, the matching circuit being configured to tune the probe for establishing the activating RF field within the container to accommodate more or fewer items in the container.

9. A method for retrofitting a container to identify and track an inventory of medical articles located in the container, the container having electrically-conductive walls within which the medical articles are located, each of the medical articles having an attached identification device that is activated by RF energy and which responds to activation by sending an identification signal, the method comprising:
mounting an RF (radio frequency) enabling module within the electrically-conductive walls of the container, the RF module comprising:
a base having a size selected to be mounted within the electrically-conductive walls of the container, the base having a data port and a power port;
a probe located on the base and configured to inject an activating RF field within the container for activating the identification devices of the medical articles located within the container;
a reader unit located on the base and having a communications unit with which it connects to the data port, the reader unit also having a control unit connected with the power port and the communications unit, the control unit configured to use power received from the power port to control the probe to inject power into the container to establish an activating RF field within the container, the control unit also configured to control the probe to stop injecting energy into the container and during the non-injection time, to receive the identification signals from the activated identification devices on the medical articles located within the electrically-conductive walls of the container, to process those signals, and to deliver data representative of the identification signals to the data port through the communications unit;
controlling the probe to inject the activating RF field into the container to activate the identification devices of the medical articles so that they will transmit identification signals;
switching off the probe from injecting the activating RF field; and
receiving by the probe RF identification signals from the activated identification devices located on the medical articles within the container.

10. The method of retrofitting a container of claim 9 further comprising powering the RF-enabling module with an Ethernet port, and exporting data representative of the processed identification signals through the Ethernet port.

11. The method of retrofitting a container of claim 9 further comprising automatically retuning the probe to establish the activating RF field to accommodate more or fewer medical articles in the container.

12. The method of retrofitting a container of claim 9 wherein the step of controlling the probe to inject the activating RF field into the container comprises injecting the activating RF field with multiple probes located on the base apart from each other, and wherein the reader unit is centrally located on the base between the multiple probes.

13. The method of retrofitting a container of claim 9 wherein the steps of controlling the probe to inject the activating RF field into the container, switching off the probe from injecting the activating RF field and receiving by the probe RF identification signals from the activated identification devices located on the medical articles within the container are performed according to a schedule.

14. The method of retrofitting a container of claim 9 wherein the step of controlling the probe to inject the activating RF field into the container comprises controlling the impedance of the probe with a matching circuit to match impedance of the container to accommodate more or fewer items in the container.

15. A method for assembling an RF (radio frequency) enabling module usable to retrofit a container to identify and track an inventory of medical articles located in the container, the container having electrically-conductive walls within which the medical articles are located, each of the medical articles having an attached identification device that is activated by RF energy and which responds to activation by sending an identification signal, the method comprising:
mounting a probe configured to inject an activating RF field within the container for activating the identification devices of the medical articles located within the container on a base, the base having a size selected to be mounted within the electrically-conductive walls of the container, the base having a data port and a power port; and
mounting a reader unit to the base, the reader unit having a communications unit with which it connects to the data port, the reader unit also having a control unit connected with the power port and the communications unit, the control unit configured to use power received from the power port to control the probe to inject power into the container to establish an activating RF field within the container, the control unit also configured to control the probe to stop injecting energy into the container and during the non-injection time, to receive the identification signals from the activated identification devices on the medical articles located within the electrically-conductive walls of the container, to process those signals, and to deliver identification data representative of the identification signals to the data port through the communications unit.

16. The method for assembling an RF (radio frequency) enabling module of claim 15 further comprising the step of configuring the module with an Ethernet port for receiving operation power from the Ethernet port and for exporting data representative of the processed identification signals through the Ethernet port.

17. The method for assembling an RF (radio frequency) enabling module of claim 15 further comprising the step of enabling automatic retuning of the probe to establish the activating RF field to accommodate or fewer medical articles in the container.

18. The method for assembling an RF (radio frequency) enabling module of claim 15 wherein the step of mounting a probe configured to inject an activating RF field within the container comprises mounting a plurality of probes to the base spaced apart from each other, each probe to inject the activating RF field into the container.

19. The method for assembling an RF (radio frequency) enabling module of claim 18 wherein the step of mounting the reader unit to the base comprises mounting the reader unit in a central location on the base between the multiple probes.

20. The method for assembling an RF (radio frequency) enabling module of claim 15 wherein the step of mounting a control unit to the base comprises configuring the control unit to control the probe to inject the activating RF field into the container, to switch off the probe from injecting the activating RF field, and to receive by the probe RF identification signals from the activated identification devices located on the medical articles within the container according to a schedule.

21. The method for assembling an RF (radio frequency) enabling module of claim 15 further comprises enabling control over the impedance of the probe with a matching circuit to match impedance of the probe with the container to accommodate more or fewer items in the container.

\* \* \* \* \*